United States Patent
Deng et al.

(10) Patent No.: US 7,446,195 B2
(45) Date of Patent: Nov. 4, 2008

(54) HIGH AFFINITY THIOPHENE-BASED AND FURAN-BASED KINASE LIGANDS

(75) Inventors: Yongqi Deng, Newton, MA (US); Lianyun Zhao, Burlington, MA (US); Gerald W. Shipps, Jr., Stoneham, MA (US); Patrick J. Curran, Winthrop, MA (US); M. Arshad Siddiqui, Newton, MA (US); Rumin Zhang, Edison, NJ (US); Charles W. McNemar, High Bridge, NJ (US); Todd W. Mayhood, Randolph, NJ (US); William T. Windsor, East Brunswick, NJ (US); Emma M. Lees, Oakland, CA (US); David A. Parry, Mountain View, CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/505,263

(22) Filed: Aug. 16, 2006

(65) Prior Publication Data

US 2007/0043045 A1    Feb. 22, 2007

Related U.S. Application Data

(60) Provisional application No. 60/709,143, filed on Aug. 17, 2005.

(51) Int. Cl.
  *C07D 413/12*   (2006.01)
  *C07D 403/12*   (2006.01)
  *C07D 409/12*   (2006.01)
  *C07D 405/12*   (2006.01)
(52) U.S. Cl. .................. 544/146; 544/152; 544/359; 546/213; 546/214; 546/280.4; 546/284.7
(58) Field of Classification Search ............... 544/112
See application file for complete search history.

(56) References Cited

U.S. PATENT DOCUMENTS 3,546,255 A    12/1970   Duennberger et al.

FOREIGN PATENT DOCUMENTS

| EP | 0 915 088 A1 | 5/1999 |
|----|--------------|--------|
| GB | 1 147 295 A | 4/1969 |
| WO | WO 01/98290 A2 | 12/2001 |
| WO | WO 02/10162 A | 2/2002 |
| WO | WO 2004/069803 A2 | 8/2004 |
| WO | WO 2004/101549 A | 11/2004 |

OTHER PUBLICATIONS

Vippagunta, et al. Advanced Drug Delivery Reviews 48 (2001) 3-26.*
Mndzhoyan, A. L. et al.,Abstract: Armyanskii Khimicheskii Zhumal, (1969), 22(10), pp. 933-935: Database Caplus Chemical Abstracts Service, XP002412638, 2pgs.
Voegtle F. et al., "Amide-Based Rotaxanes with Terephthal Furan, Thiopene and Sulfonamide Subunits", Synthesis (1996), vol. 3, pp. 353-356. XP002412666.
International Search Report for International Application No. PCT/US2006/031973, mailed Jan. 10, 2007 (5pgs).

* cited by examiner

*Primary Examiner*—Shawquia Young
(74) *Attorney, Agent, or Firm*—Palaiyur S. Kalyanaraman

(57) ABSTRACT

Inhibitors of cyclin dependent kinase 2, compositions including the inhibitors, and methods of using the inhibitors and inhibitor compositions are described. The inhibitors and compositions including them are useful for treating disease or disease symptoms. The invention also provides for methods of making CDK-2 inhibitor compounds, methods of inhibiting CDK-2, and methods for treating disease or disease symptoms.

10 Claims, No Drawings

HIGH AFFINITY THIOPHENE-BASED AND FURAN-BASED KINASE LIGANDS

REFERENCE TO PRIORITY APPLICATION

This application claims benefit of priority from U.S. provisional patent application Ser. No. 60/709,143 filed Aug. 17, 2005.

FIELD OF THE INVENTION

The present invention relates to novel compounds useful as protein kinase inhibitors (such as for example, the inhibitors of the cyclin-dependent kinases, mitogen-activated protein kinase (MAPK/ERK), glycogen synthase kinase 3(GSK3beta) and the like), pharmaceutical compositions containing the compounds, and methods of treatment using the compounds and compositions to treat diseases such as, for example, cancer, inflammation, arthritis, viral diseases, neurodegenerative diseases such as Alzheimer's disease, cardiovascular diseases, and fungal diseases. The compounds disclosed herein are especially useful as cyclin dependent kinase inhibitors, such as, for example, CDK-1 and CDK-2 inhibitors.

BACKGROUND OF THE INVENTION

Cell growth and differentiation is a highly controlled process which, when uncontrolled, can lead to aberrant cell function, often resulting in a disease state. Protein phosphorylation is one of the main post translational mechanisms used to control cellular function. Protein kinases catalyze the phosphorylation of serine, threonine and tyrosine residues using either ATP or GTP. An analysis of the human genome has revealed that there are predicted to be ~500 protein kinases (Manning G., Whyte D. B., Martinez R., Hunter T., Sudarsanam S., Science 298, 1912, 2002; Kostich M, English J, Madison V, Gheyas F, Wang L, Qiu P, Greene J, Laz T M., Genome Biol. 3(9), 2002). When phosphorylation regulation by these kinases is lost, a number of diseases may occur, including diabetes, Alzheimer's, inflammation, and cancer (Cohen P., Eur. J. Biochem. 268, 5001-5010, 2001; Cohen P., Nat. Rev. Drug Discovery 1, 309-315, 2002.)

Multiple cellular signals can stimulate growth, differentiation, and apoptosis, and a key mechanism for regulating these processes involves the cell cycle, which controls cell division by regulating passage through the G1, S, G2, and M phases of DNA synthesis and mitosis. Progression through the eukaryotic cell cycle is controlled by the cyclin dependent kinase (CDK) family of kinases. CDKs are primarily serine/threonine kinases and they bind to several different regulatory subunits called cyclins. Different CDK/cyclin heterodimers regulate a variety of processes in the cell cycle, thus, it is believed that CDK-4/cyclin D and CDK-2/cyclin E regulate control through G1 into the onset of the S phase. The down regulation of cyclin D and cyclin E and the up regulation of cyclin A to form heterodimers with CDK-2 and CDK-1 promotes passage through the S-phase into G2. Finally, activated complexes of CDK-1 (Cdc2)/cyclin B and possibly CDK-1 (Cdc2)/cyclin A are thought to promote the transition from G2 into the M-phase (reviewed by Murray A., Cell 116, 221-234, 2004). Some of the known substrates for the CDKs are the tumor suppressor retinoblastoma protein (RB) and related family members p107 and p130 (Grana X., Garriga J., and Mayol X., Oncogene 17, 3365-3383, 1998). Phosphorylation of RB by CDK-4 or CDK-2 induces the release of E2F transcription factors which in turn promote the expression of regulatory proteins to stimulate cell cycle progression and cell growth. In human tumors, the control of the RB function has been observed to be disrupted through mutation of the RB gene, CDK-4 amplification, cyclin D and cyclin E over expression, inactivation of the CDK-4 specific protein inhibitor p16INK4A and a disruption in the level of the CDK inhibitor p27KIP1 (Sherr, C., Roberts J., Genes Dev. 13, 1501-1512, 1999; Hall M., Peters G., Adv. Cancer Res. 68, 67-108, 1996; Stewart T., Wesfall M., Pietenpol J., Trends Pharmacol. Sci. 24, 139-145, 2003). These functional disruptions are believed to contribute to the development of breast, colon, gastric, prostate, nonsmall cell lung, ovarian and other human cancers (Tsihlias J., Kapusta L., Slingerland J., Annu. Rev. Med. 50, 401-423, 1999; Lloyd R., Erickson L., Jin L., Kulig E., Qian X., Cheville J., Scheithauser B., Am. J. Pathol. 154(4), 313-323, 1999).

The fact that uncontrolled regulation of the cell cycle pathway is thought to be a source of human cancers leads one to believe that inhibition of unregulated CDK activity by small molecule inhibitors would be beneficial in the treatment of cancers. A large number of chemical synthesis efforts have been directed toward developing CDK specific ATP competitive inhibitors but only a few molecules have progressed into human clinical trials. These include flavopiridol, roscovitine (CYC-202) and the 2-aminothiazole derivative BMS-387032 (Zhai, S., Senderowicz A., Sausville E., Figg W., Ann. Pharmacother. 36, 905-911, 2002; McClue S., Blake D., Clarke R., Cummings L., Fischer P., MacKenzie M., Stewart K., Wang S., Zhelev N., Zheleva D., Lane D., Int. J. Cancer 102(5), 463-468, 2002; Misra R et. al., J. Med. Chem. 47, 1719-1728, 2004)

There is a need to develop CDK inhibitors for the treatment of human diseases, therefore, it is an objective of this invention to describe compounds that would be useful for the prevention or alteration of these diseases.

SUMMARY OF THE INVENTION

The invention relates to novel compounds and compositions including those compounds as well as methods of using the compounds. The compounds are heterocyclic molecules that are useful in therapeutic applications which involve CDK-2, including modulation of disease or disease symptoms in a subject (for example, cat, dog, horse, or human). These diseases include Alzheimer's disease, cancer, diabetes, and inflammation. The compounds (including stereoisomers thereof) are synthesized either individually or in a combinatorial fashion to give structurally and stereochemically diverse libraries of compounds.

CDK-2 inhibition by the compounds included in this invention was demonstrated and quantified by measuring the binding affinity (Ki) between these compounds and CDK-2 using a fluorescence polarization displacement assay. In certain embodiments, the compounds are thiophene compounds that are substituted with aryl amido moieties. In one embodiment, provided herein are compounds of formula 1:

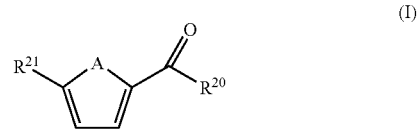

or a pharmaceutically acceptable salt, solvate or ester thereof, wherein

A is O or S;
R$^{20}$ is:

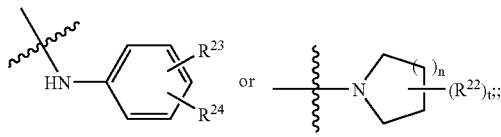

R$^{21}$ is —C(O)N(R$^{25}$R$^{26}$) or —N(R$^{26}$)C(O)R$^{25}$;
R$^{22}$ is hydrogen, alkyl, oxo, amido, cyano, aryl, heteroaryl, heterocyclyl, aryloxy, heteroaryloxy, or heterocyclyloxy;
R$^{23}$ is hydrogen, alkyl, alkoxy, alkoxyalkylamino, amino, alkylamino, dialkylamino, alkylheterocyclyl, alkylaryl, alkylheteroaryl, amido, aryl, alkoxyoxo, halo, heteroaryl, heterocyclyl, cyano, oxo, or aminoalkyl, wherein each of said alkyl, alkoxy, alkoxyalkylamino, amino, alkylamino, dialkylamino, alkylheterocyclyl, alkylaryl, alkylheteroaryl, aryl, alkoxyoxo, heteroaryl, heterocyclyl and aminoalkyl is either unsubstituted or optionally independently substituted with 1-3 independently selected P$^{1}$ substituents, where P$^{1}$ is alkyl, aryl, heteroaryl, heterocyclyl, cycloalkyl, alkoxy, amino, alkylamino, dialkylamino, or alkylthio, or two P$^{1}$ adjacent moieties together form an alkylenedioxy moiety fused to said aryl, heteroaryl, heterocyclyl ring they are attached to;
R$^{24}$ is hydrogen, halo, alkyl, alkylene, lower alkyl, aryl, heteroaryl, heterocyclyl, alkoxy, amino, aminoalkyl, alkylamino, dialkylamino, alkylthio, trihaloalkyl, wherein each of said alkyl, alkylene, lower alkyl, aryl, heteroaryl, heterocyclyl, alkoxy, amino, aminoalkyl, alkylamino, dialkylamino, alkylthio, trihaloalkyl is either unsubstituted or optionally independently substituted with 1-3 independently selected P$^{1}$ substituents, where P$^{1}$ is alkyl, aryl, heteroaryl, heterocyclyl, cycloalkyl, alkoxy, amino, alkylamino, dialkylamino, or alkylthio; or two R$^{24}$ groups, which substitute atoms in a 1,2 or 1,3 arrangement on the phenyl ring said R$^{24}$ is shown attached to together form —O—(CH$_{2}$)$_{y}$—O—, —S—(CH$_{2}$)$_{y}$—O—, —S—(CH$_{2}$)$_{y}$—S, —CH=CH—CH=N—, —N=CH—CH=N—, or —S—CH=N— where y is 1 or 2;
or alternately R$^{23}$ and R$^{24}$ together form an aryl, heteroaryl or heterocyclyl ring with said aryl, heteroaryl or heterocyclyl ring being fused to the phenyl ring they are shown attached to;
R$^{25}$ is hydrogen, alkyl, aryl, arylalkyl, heteroaryl, heteroarylalkyl, cycloalkyl, heterocyclyl, alkylheterocyclyl, or alkoxyaryl, wherein each of said alkyl, aryl, arylalkyl, heteroaryl, heteroarylalkyl, cycloalkyl, heterocyclyl, alkylheterocyclyl, and alkoxyaryl is either unsubstituted or optionally independently substituted with 1-3 independently selected Q$^{1}$ substituents, where Q$^{1}$ is alkyl, cycloalkyl, alkoxy, aryl, aryloxy, heterocyclyl, heterocyclyloxy, heteroaryl, heteroaryloxy, halo, hydroxy, oxo, amino, heterocyclyl amino, aminoalkyl, alkylamino, dialkylamino, trifluoroalkyl, sulfonamide, 4-6 membered lactone ring, or alkylenedioxy wherein each Q$^{1}$ is unsubstituted or optionally independently substituted with one or more substituents independently selected from the group consisting of alkyl, cycloalkyl, alkoxy, aryl, aryloxy, heterocyclyl, heterocyclyloxy, heteroaryl, heteroaryloxy, halo, hydroxy, oxo, amino, heterocyclyl amino, aminoalkyl, alkylamino, and dialkylamino;
R$^{26}$ is hydrogen, alkyl or lower alkyl;
or alternately R$^{25}$ and R$^{26}$ can be linked together to form aryl, cycloalkyl, heterocyclyl or heteroaryl;
n is 1 or 2; and
t is 1 or 2.

In one embodiment, the groups R$^{20}$, R$^{2}$, R$^{22}$, R$^{23}$, R$^{24}$, R$^{25}$, and R$^{26}$, n, t etc. are selected such that the resulting compound has an inhibitory effect on CDK-2.

Some embodiments include pharmaceutically-acceptable derivatives, including salts, esters, enol ethers, enol esters, solvates, hydrates and prodrugs of the compounds described herein.

Pharmaceutical compositions formulated for administration by an appropriate route and means containing effective concentrations of one or more of the compounds provided herein, or pharmaceutically acceptable derivatives thereof, that deliver amounts effective for the treatment, prevention, or amelioration of one or more symptoms of diseases or disorders that are modulated or otherwise affected by CDK-2, are also provided. The effective amounts and concentrations are effective for ameliorating any of the symptoms of any of the diseases or disorders. Methods of treatment, prevention, or amelioration of one or more symptoms of a disease or disorder that is modulated or otherwise affected by CDK-2 is implicated, are provided. Such methods include methods of treatment, prevention and amelioration of one or more symptoms of inflammatory disease, neurodegenerative disease, cancer and diabetes using one or more of the compounds provided herein, or pharmaceutically acceptable derivatives thereof. Non-limiting examples of inflammatory disease are acute pancreatitis, chronic pancreatitis, asthma, allergies, and adult respiratory distress syndrome. Non-limiting examples of neurodegenerative disease are acute Alzheimer's disease, Parkinson's disease, cerebral ischemia, and other neurodegenerative diseases. Non-limiting examples of the diabetes are diabetes mellitus and diabetes insipidus, e.g., type 1 diabetes and type 2 diabetes.

In practicing the methods, effective amounts of the compounds or compositions containing therapeutically effective concentrations of the compounds, which are formulated for systemic delivery, including parenteral, oral, or intravenous delivery, or for local or topical application, for the treatment of CDK-2 mediated diseases or disorders, including, but not limited to, inflammatory diseases, neurodegenerative diseases, cancer and diabetes, are administered to an individual exhibiting the symptoms of these diseases or disorders. The amounts are effective to ameliorate or eliminate one or more symptoms of the diseases or disorders.

Articles of manufacture containing packaging material, a compound or composition, or pharmaceutically acceptable derivative thereof, provided herein, which is effective for modulating the activity of CDK-2, mediated diseases or disorders are provided, within the packaging material, and a label that indicates that the compound or composition, or pharmaceutically acceptable derivative thereof, is used for modulating the activity of CDK-2, mediated diseases or disorders, are provided.

DETAILED DESCRIPTION

A. Definitions

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there is a plurality of definitions for a term herein, those in this section prevail unless stated otherwise.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. In certain embodiments, salt forms of the compounds improve the compounds dissolution rate and oral bioavailability.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkenylene" means a difunctional group obtained by removal of a hydrogen from an alkenyl group that is defined above. Non-limiting examples of alkenylene include —CH═CH—, —C(CH$_3$)═CH—, and —CH═CHCH$_2$—.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), Y$^1$Y$^2$N—, Y$^1$Y$^2$N-alkyl-, Y$^1$Y$^2$NC(O)—, Y$^1$Y$^2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

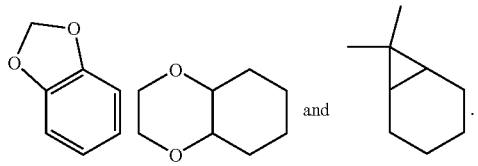

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system. Example of such moiety is pyrrolidone:

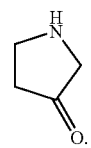

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

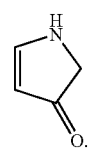

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

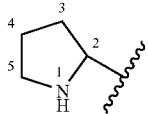

there is no —OH attached directly to carbons marked 2 and 5.

It should also be noted that tautomeric forms such as, for example, the moieties:

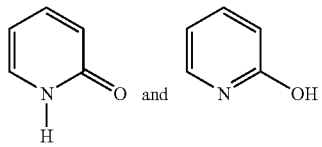

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula 1, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-($(C_1-C_6)$alkanoyloxy)ethyl, 1-methyl-1-($(C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)O$Y^1$ wherein $Y^1$ is H, $(C_1-C_6)$alkyl or benzyl, —C(O$Y^2$)$Y^3$ wherein $Y^2$ is $(C_1-C_4)$ alkyl and $Y^3$ is $(C_1-C_6)$alkyl, carboxy $(C_1-C_6)$alkyl, amino $(C_1-C_4)$alkyl or mono-N- or di-N,N-$(C_1-C_6)$alkylaminoalkyl, —C($Y^4$)$Y^5$ wherein $Y^4$ is H or methyl and $Y^5$ is mono-N— or di-N,N-$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, J. Pharmaceutical Sci., 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula I, and salts, solvates, esters and prodrugs thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all ketoenol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I, and of the salts, solvates, esters and prodrugs of the compounds of Formula I, are intended to be included in the present invention.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

As used herein, "substituted alkyl," "substituted alkenyl," "substituted alkynyl," "substituted cycloalkyl," "substituted cycloalkenyl," "substituted cycloalkynyl," "substituted aryl," "substituted heteroaryl," "substituted heterocyclyl," "substituted alkylene," "substituted alkenylene," "substituted alkynylene," "substituted cycloalkylene," "substituted cycloalkenylene," "substituted cycloalkynylene," "substituted arylene," "substituted heteroarylene" and "substituted heterocyclylene" refer to alkyl, alkenyl, alkynyl, cycloalkyl, cycloalkenyl, cycloalkynyl, aryl, heteroaryl, heterocyclyl, alkylene, alkenylene, alkynylene, cycloalkylene, cycloalkenylene, cycloalkynylene, arylene, heteroarylene and heterocyclylene groups, respectively, that are substituted with one or more substituents, in certain embodiments one, two, three or four substituents, where the substituents are as defined herein, for example, in one embodiment selected from $P^1$.

As used herein, "amido" refers to the divalent group —C(O)NH—. "Thioamido" refers to the divalent group —C(S)NH—. "Oxyamido" refers to the divalent group —OC(O)NH—. "Thiaamido" refers to the divalent group —SC(O)NH—. "Dithiaamido" refers to the divalent group —SC(S)NH—. "Ureido" refers to the divalent group —HNC(O)NH—. "Thioureido" refers to the divalent group —HNC(S)NH—.

As used herein, "haloalkoxy" refers to RO— in which R is a haloalkyl group.

As used herein, "heterocyclyloxy", refers to RO— in which R is a heterocyclyl group, heteroaryloxy refers to RO— in which R is a heteroaryl group.

Where the number of any given substituent is not specified (e.g., haloalkyl), there may be one or more substituents present. For example, "haloalkyl" may include one or more of the same or different halogens. As another example, "$C_{1-3}$alkoxyphenyl" may include one or more of the same or different alkoxy groups containing one, two or three carbons.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, $IC_{50}$ refers to an amount, concentration or dosage of a particular test compound that achieves a 50% inhibition of a maximal response, such as modulation of CDK-2 kinase activity, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) Biochem. 11:942-944). Certain of the abbreviations used herein are listed below:

B. Compounds

In one embodiment, the compounds provided herein for use in the compositions and methods provided herein have formula 1, where the variables are as described below. All combinations of such embodiments are within the scope of the instant disclosure.

In one embodiment, $R^{20}$ is:

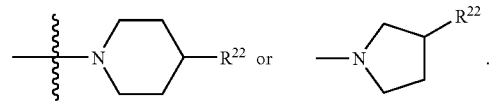

In another embodiment, $R^{22}$ is:

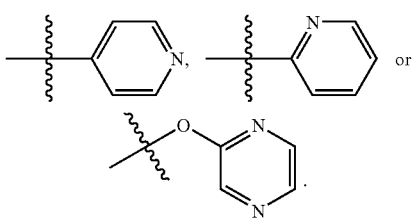

In another embodiment, $R^{20}$ is

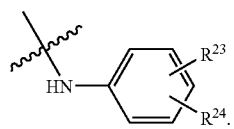

In another embodiment, $R^{23}$ is hydrogen, alkyl, alkoxy, alkoxyalkylamino, amino, alkylamino, dialkylamino, alkylheterocyclyl, alkylaryl, alkylheteroaryl, amido, aryl, alkoxyoxo, halo, heteroaryl, heterocyclyl, cyano, oxo, or aminoalkyl wherein each of said alkyl, alkoxy, alkoxyalkylamino, amino, alkylamino, dialkylamino, alkylheterocyclyl, alkylaryl, alkylheteroaryl, aryl, alkoxyoxo, heteroaryl, heterocyclyl and aminoalkyl is either unsubstituted or optionally independently substituted with 1-3 independently selected $P^1$ substituents, where $P^1$ is alkyl, aryl, heteroaryl, heterocyclyl, cycloalkyl, alkoxy, amino, alkylamino, dialkylamino, or alkylthio, or two $P^1$ adjacent moieties together form an alkylenedioxy moiety fused to said aryl, heteroaryl, heterocyclyl ring they are attached to.

In another embodiment, $R^{23}$ is

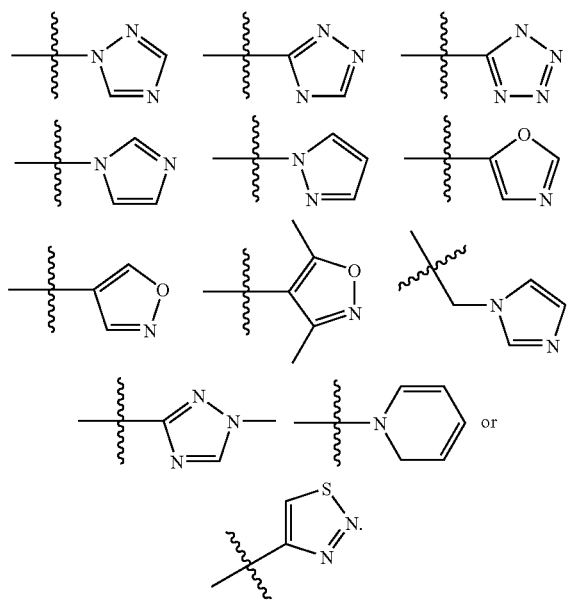

In another embodiment, $R^{23}$ is

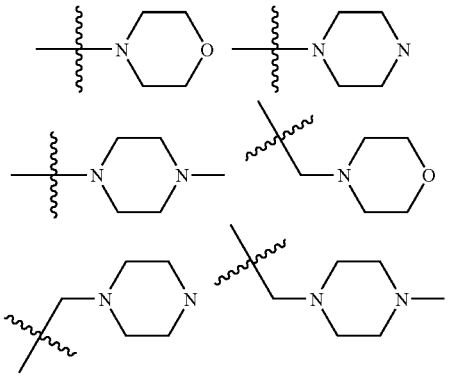

-continued

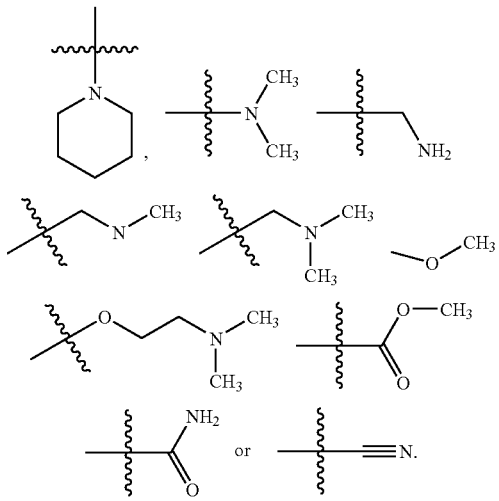

In another embodiment, $R^{24}$ is hydrogen, halo, alkyl, alkylene, lower alkyl, aryl, heteroaryl, heterocyclyl, alkoxy, amino, aminoalkyl, alkylamino, dialkylamino, alkylthio, trihaloalkyl, wherein each of said alkyl, alkylene, lower alkyl, aryl, heteroaryl, heterocyclyl, alkoxy, amino, aminoalkyl, alkylamino, dialkylamino, alkylthio, trihaloalkyl is unsubstituted or optionally independently substituted with 1-3 independently selected $P^1$ substituents, where $P^1$ is alkyl, aryl, heteroaryl, heterocyclyl, cycloalkyl, alkoxy, amino, alkylamino, dialkylamino, or alkylthio; or two $R^{24}$ groups, which substitute atoms in a 1,2 or 1,3 arrangement on the phenyl ring said $R^{24}$ is shown attached to together form —O—$(CH_2)_y$—O—, —S—$(CH_2)_y$—O—, —S—$(CH_2)_y$—S, —CH=CH—CH=N—, —N=CH—CH=N—, or —S—CH=N— where y is 1 or 2.

In another embodiment, $R^{23}$ and $R^{24}$ together form a ring moiety with said ring moiety being fused to the phenyl ring they are shown attached to, such that $R^{20}$ becomes:

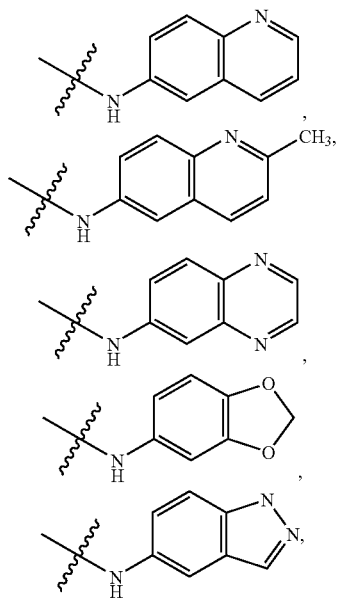

-continued

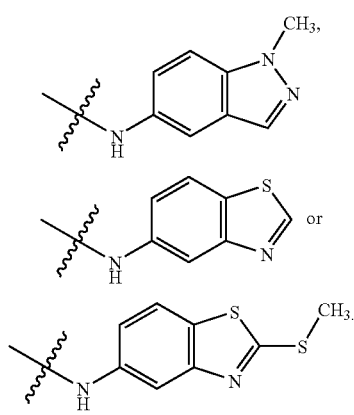

In another embodiment, R$^{25}$ is hydrogen, alkyl, aryl, arylalkyl, heteroaryl, heteroarylalkyl, cycloalkyl, heterocyclyl, alkylheterocyclyl, or alkoxyaryl, wherein each of said alkyl, aryl, arylalkyl, heteroaryl, heteroarylalkyl, cycloalkyl, heterocyclyl, alkylheterocyclyl, and alkoxyaryl is either unsubstituted or optionally independently substituted with 1-3 independently selected Q$^1$ substituents, where Q$^1$ is alkyl, cycloalkyl, alkoxy, aryl, aryloxy, heterocyclyl, heterocyclyloxy, heteroaryl, heteroaryloxy, halo, hydroxy, oxo, amino, heterocyclyl amino, aminoalkyl, alkylamino, dialkylamino, trifluoroalkyl, sulfonamide, 4-6 membered lactone ring, or alkylenedioxy wherein each Q$^1$ is unsubstituted or optionally independently substituted with one or more substituents independently selected from the group consisting of alkyl, cycloalkyl, alkoxy, aryl, aryloxy, heterocyclyl, heterocyclyloxy, heteroaryl, heteroaryloxy, halo, hydroxy, oxo, amino, heterocyclyl amino, aminoalkyl, alkylamino, and dialkylamino.

In another embodiment, R$^{25}$ is:

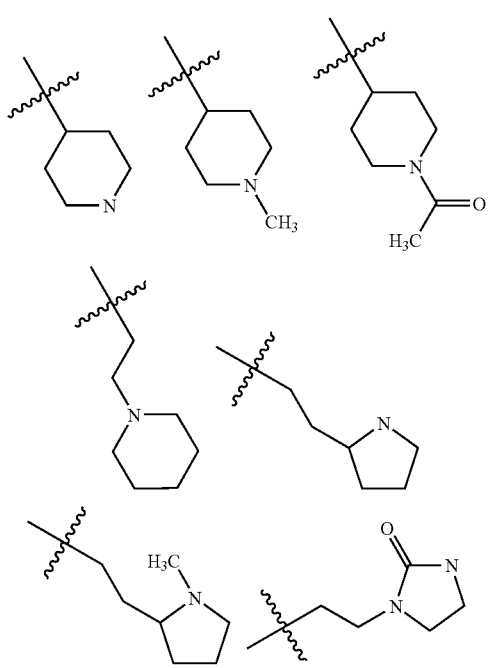

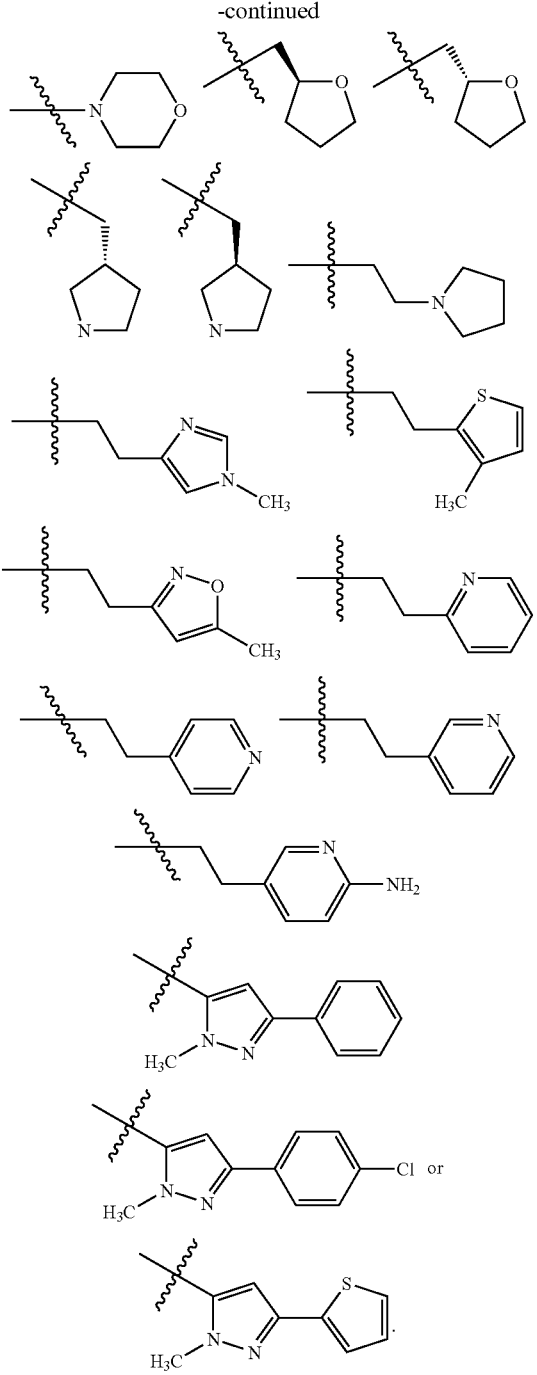

In another embodiment, R$^{25}$ is:

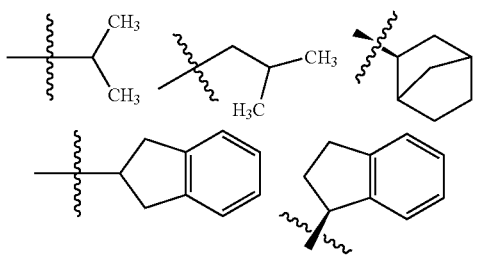

-continued
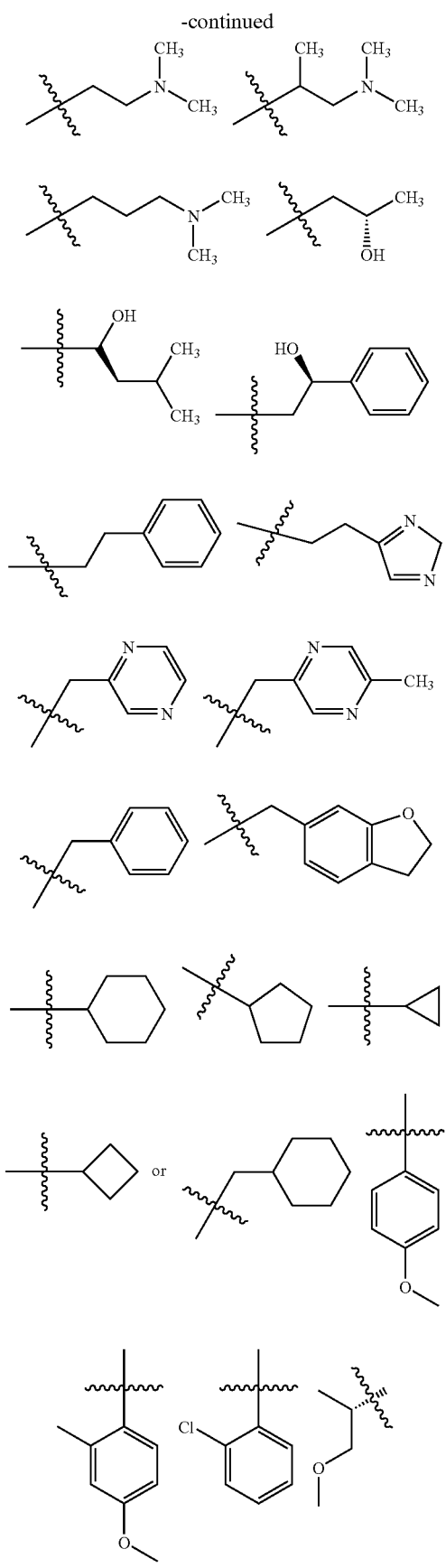
-continued
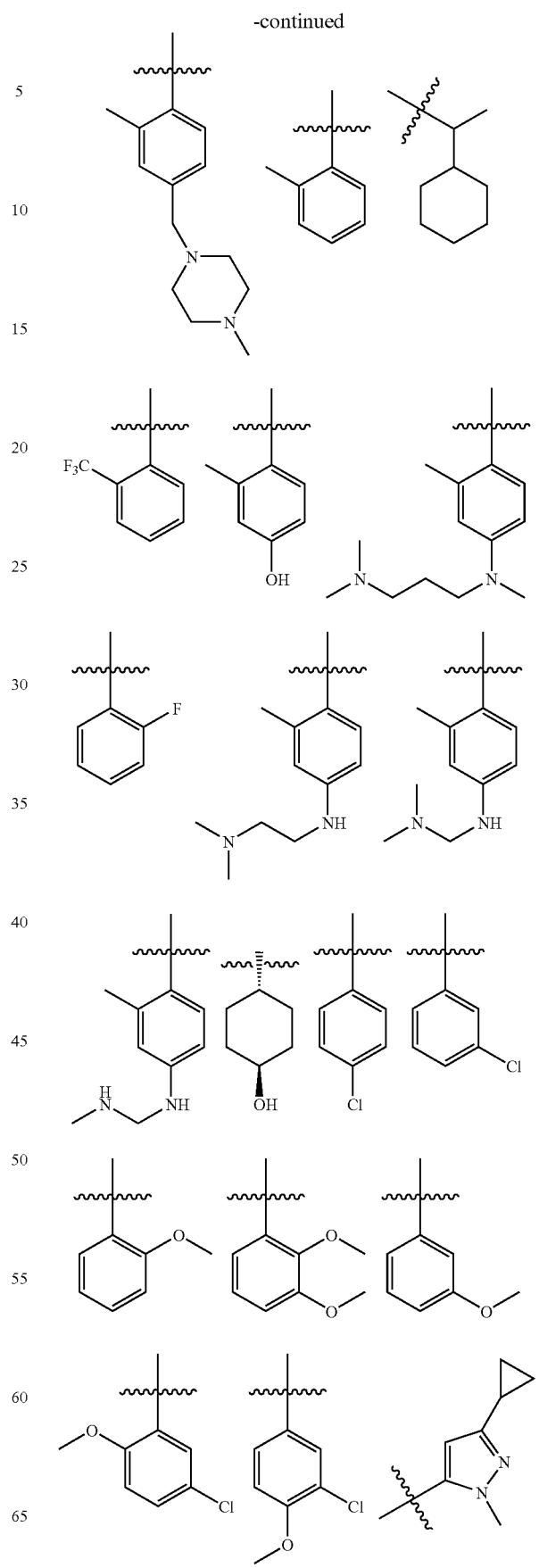

-continued
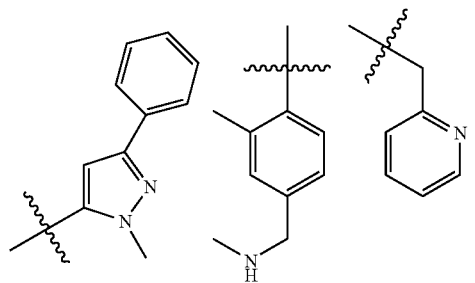
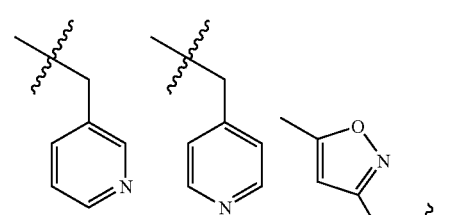
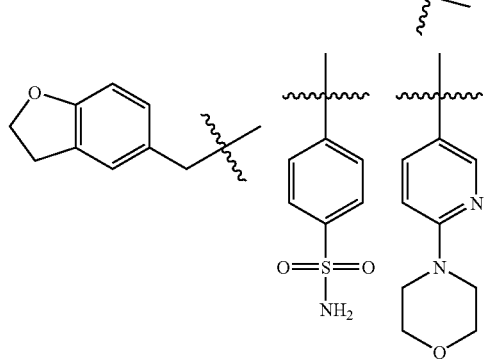
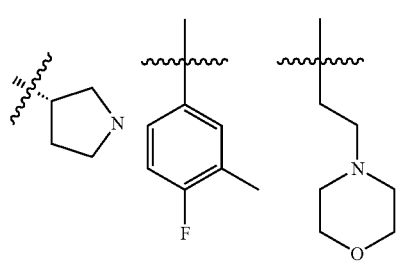
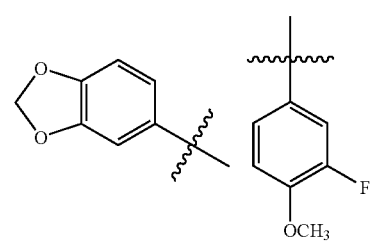
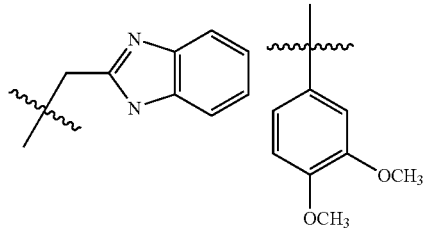
-continued
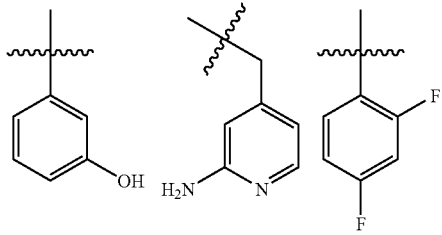
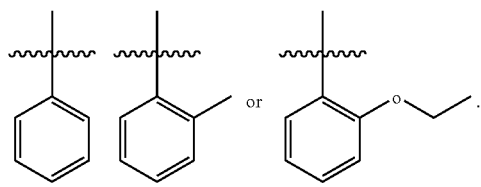
In another embodiment, $R^{25}$ is:
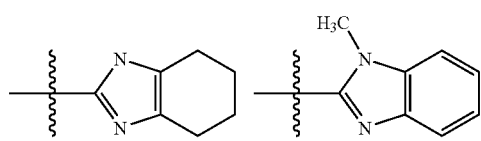
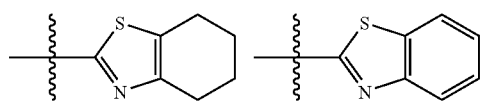
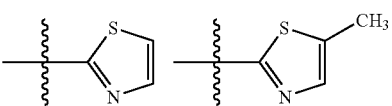
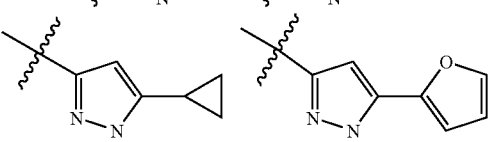
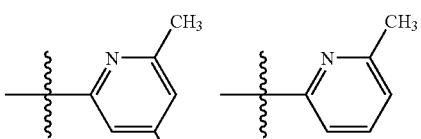
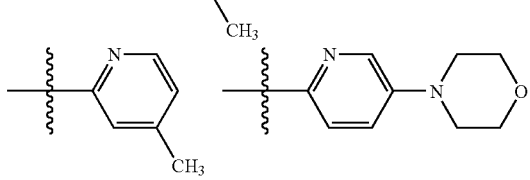
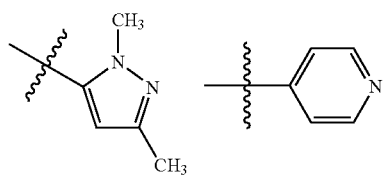
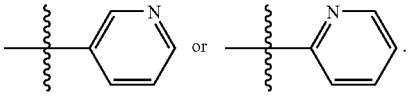

In another embodiment, R$^{25}$ is:
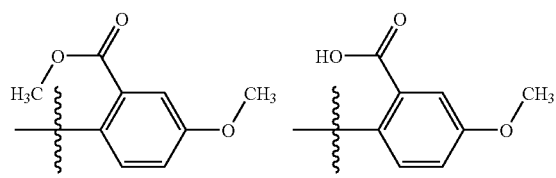
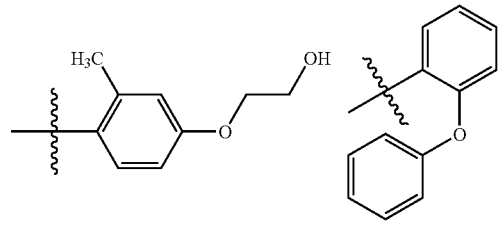
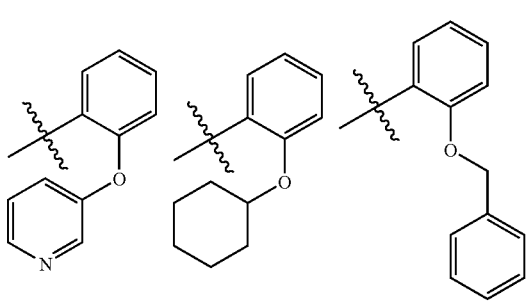
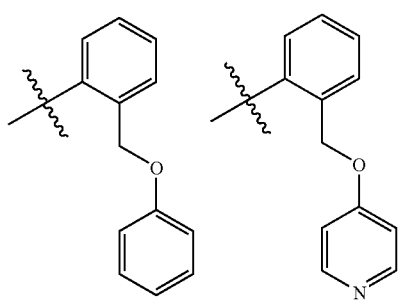
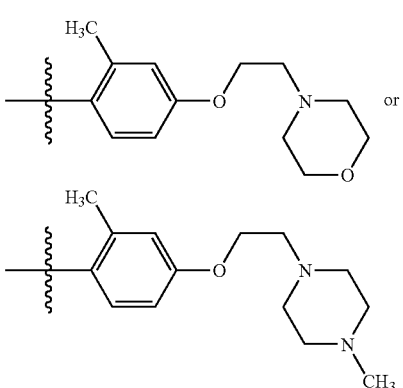
or
In another embodiment, R$^{25}$ is:
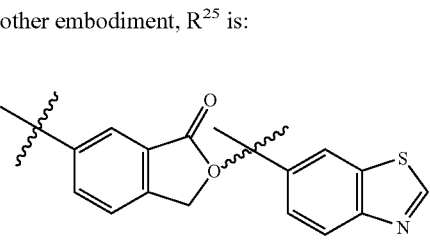
-continued
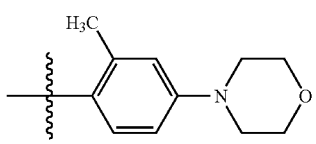
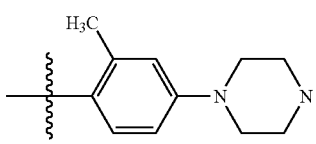
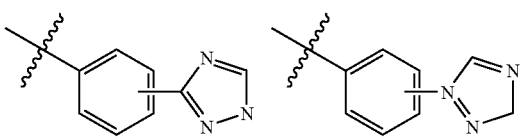
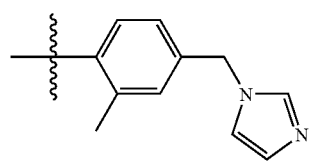
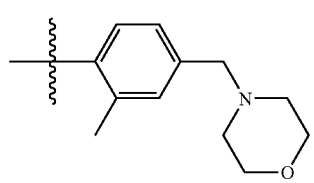
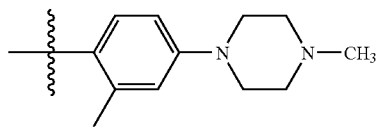
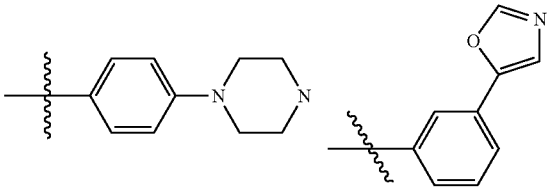
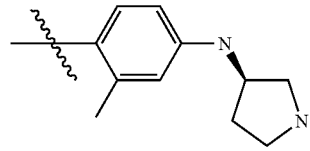
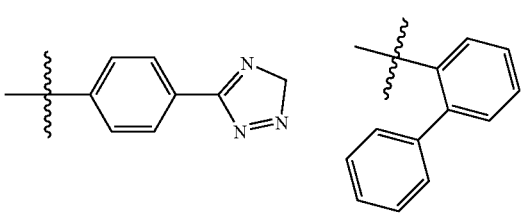

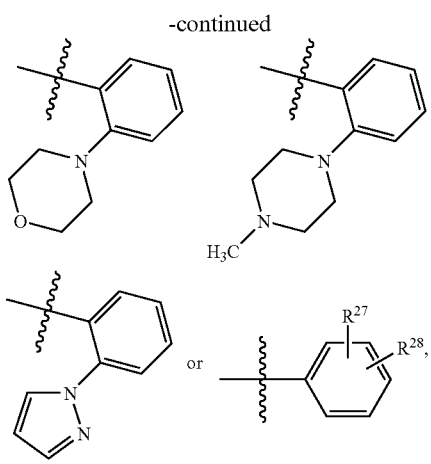

where R$^{27}$ is H, halo, or lower alkyl; and

R$^{28}$ is aryl, heteroaryl, arylalkyl, alkylheteroaryl, heterocyclyl, or alkylheterocyclyl.

In another embodiment, R$^{25}$ and R$^{26}$ are linked together to form aryl, cycloalkyl, heterocyclyl or heteroaryl, and R$^{21}$ is:

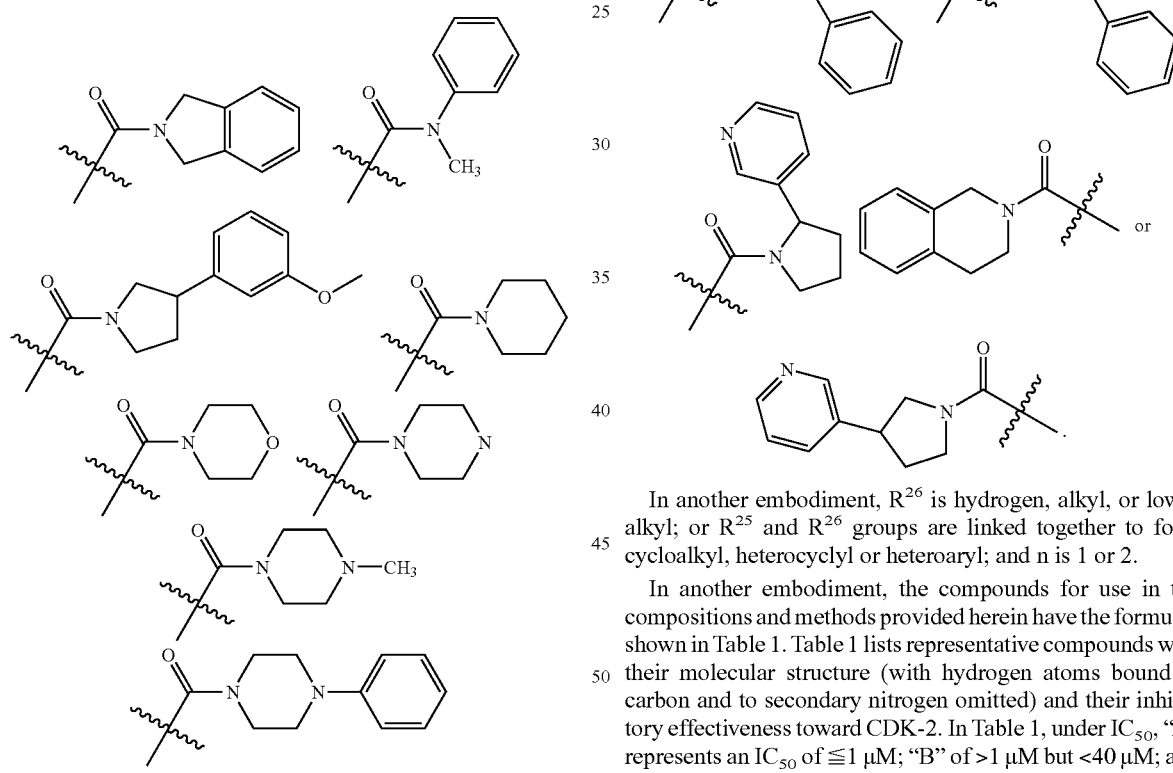

In another embodiment, R$^{26}$ is hydrogen, alkyl, or lower alkyl; or R$^{25}$ and R$^{26}$ groups are linked together to form cycloalkyl, heterocyclyl or heteroaryl; and n is 1 or 2.

In another embodiment, the compounds for use in the compositions and methods provided herein have the formulae shown in Table 1. Table 1 lists representative compounds with their molecular structure (with hydrogen atoms bound to carbon and to secondary nitrogen omitted) and their inhibitory effectiveness toward CDK-2. In Table 1, under IC$_{50}$, "A" represents an IC$_{50}$ of $\leq$1 µM; "B" of >1 µM but <40 µM; and "C" of $\geq$40 µM.

TABLE 1

Representative Compounds of the Invention

| Compound Number | STRUCTURE | IC$_{50}$ |
|---|---|---|
| 1 | 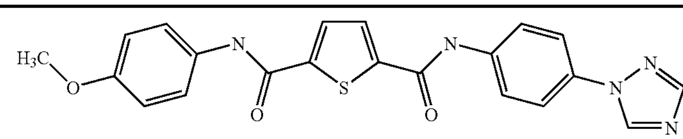 | — |

TABLE 1-continued
Representative Compounds of the Invention
| Compound Number | STRUCTURE | IC$_{50}$ |
|---|---|---|
| 2 | 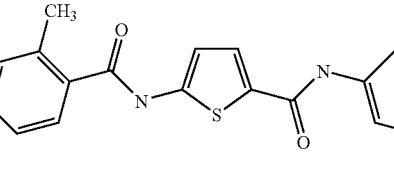 | A |
| 3 | 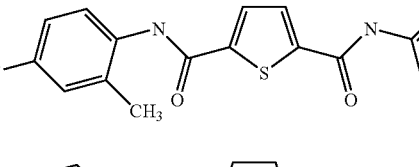 | A |
| 4 | 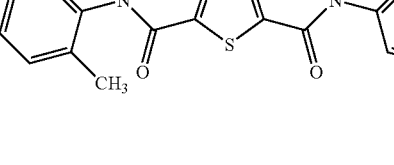 | A |
| 5 | 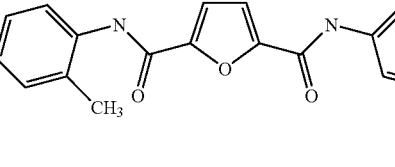 | A |
| 6 | 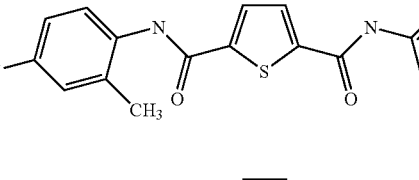 | A |
| 7 | 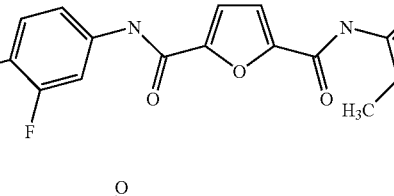 | A |
| 8 | 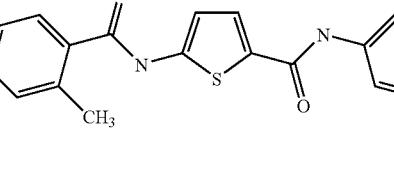 | A |
| 9 | 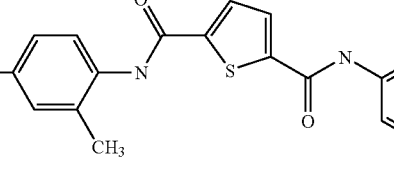 | A |

TABLE 1-continued

Representative Compounds of the Invention

| Compound Number | STRUCTURE | IC$_{50}$ |
|---|---|---|
| 10 | 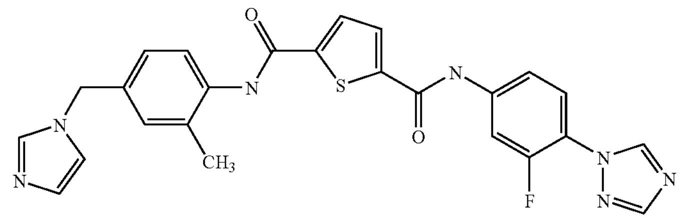 | A |
| 11 | 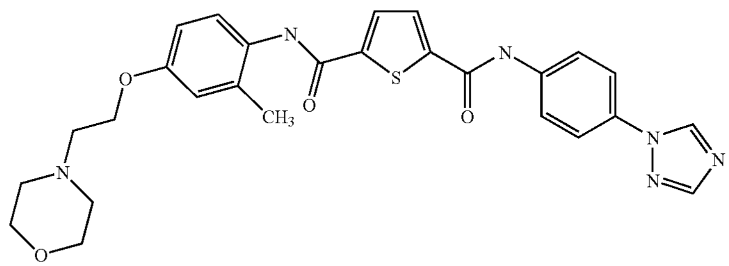 | A |
| 12 | 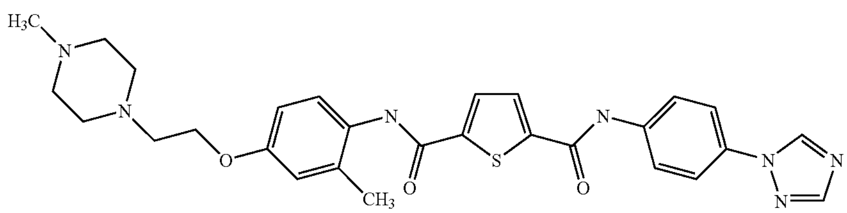 | A |
| 13 | 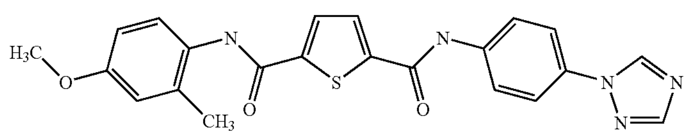 | A |
| 14 | 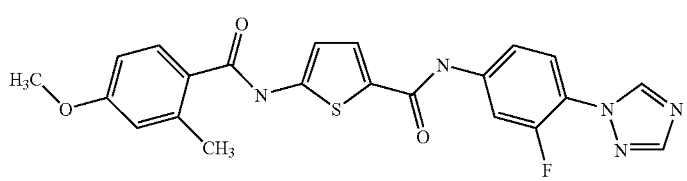 | A |
| 15 | 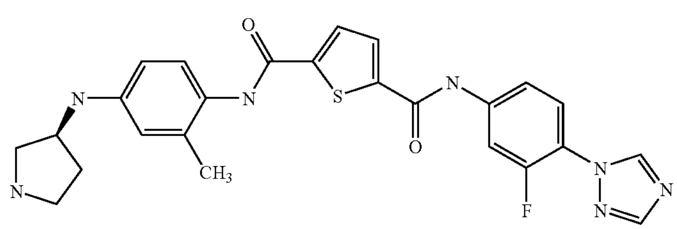 | A |
| 16 | 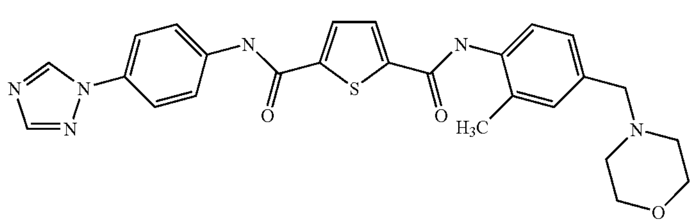 | A |

TABLE 1-continued

Representative Compounds of the Invention

| Compound Number | STRUCTURE | IC$_{50}$ |
|---|---|---|
| 17 | 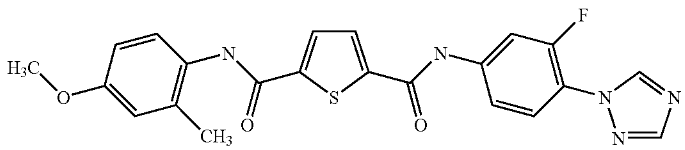 | A |
| 18 | 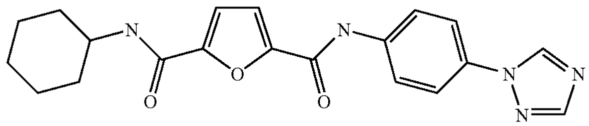 | A |
| 19 | 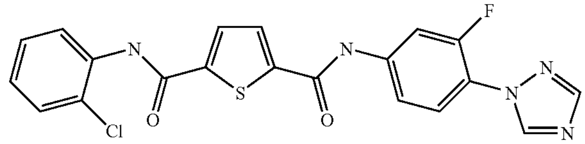 | A |
| 20 | 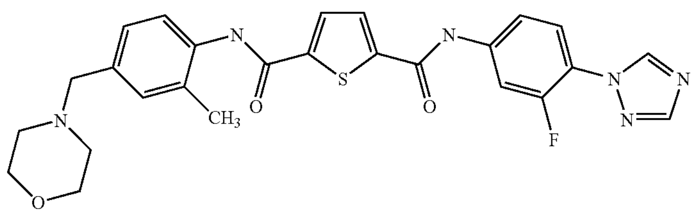 | A |
| 21 | 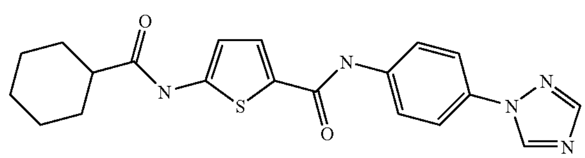 | A |
| 22 | 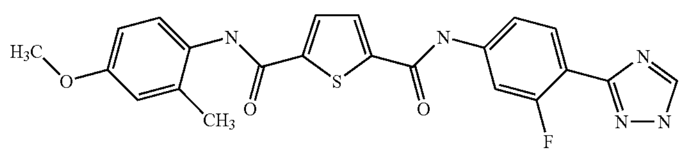 | A |
| 23 | 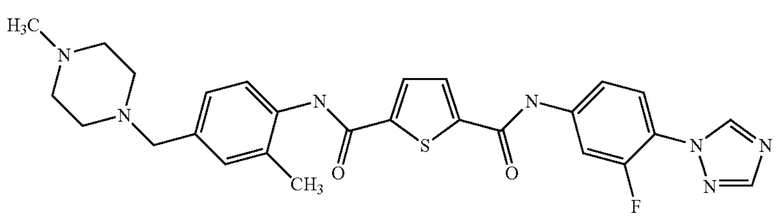 | A |
| 24 | 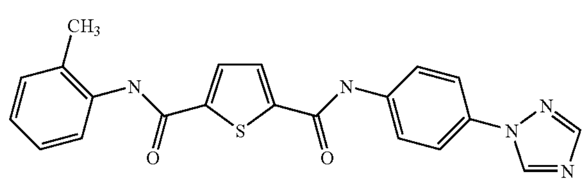 | A |
| 25 | 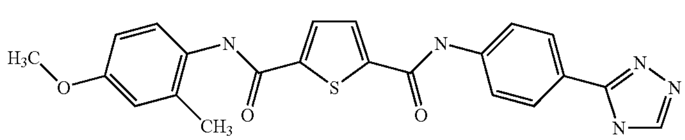 | A |

TABLE 1-continued
Representative Compounds of the Invention
| Compound Number | STRUCTURE | IC$_{50}$ |
|---|---|---|
| 26 | 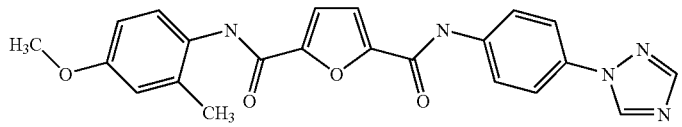 | A |
| 27 | 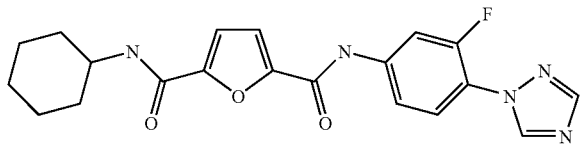 | A |
| 28 | 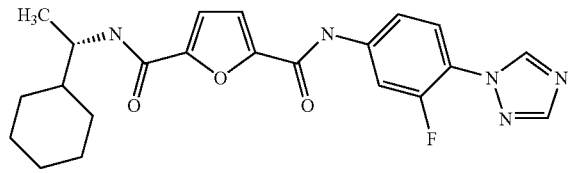 | A |
| 29 | 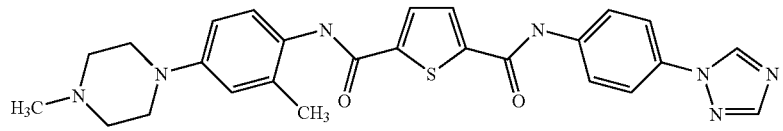 | A |
| 30 | 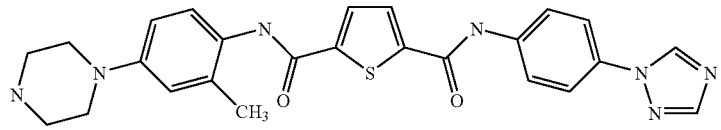 | A |
| 31 | 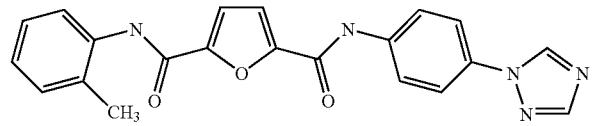 | A |
| 32 | 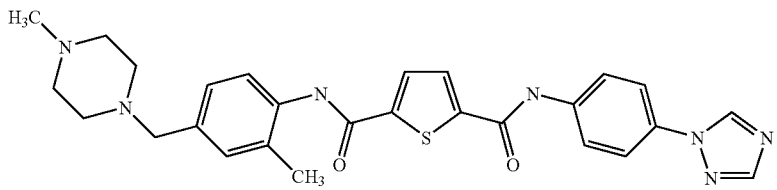 | A |
| 33 | 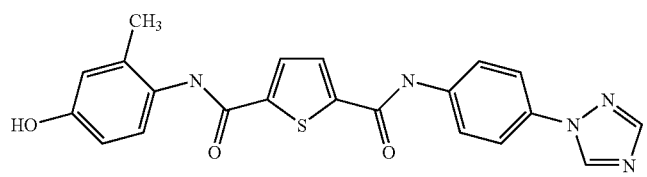 | A |
| 34 | 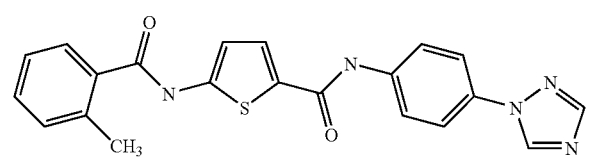 | A |

TABLE 1-continued

Representative Compounds of the Invention

| Compound Number | STRUCTURE | IC$_{50}$ |
|---|---|---|
| 35 | 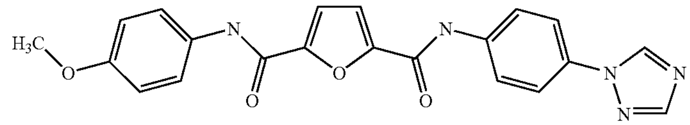 | A |
| 36 | 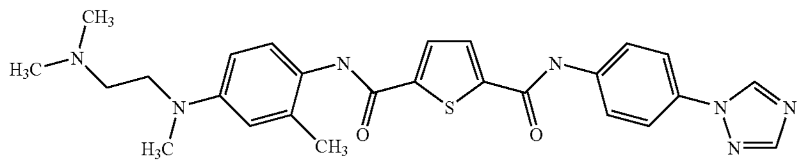 | A |
| 37 | 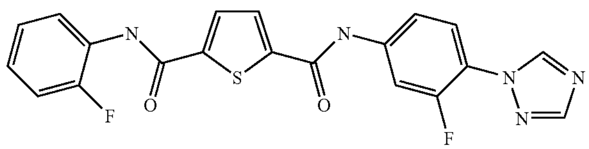 | A |
| 38 | 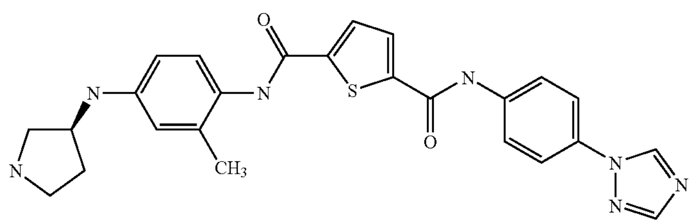 | A |
| 39 | 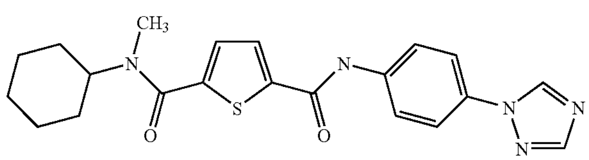 | A |
| 40 | 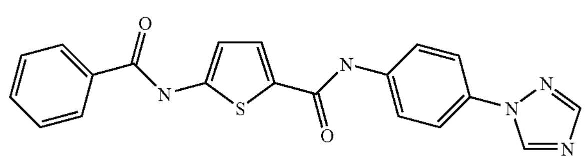 | A |
| 41 | 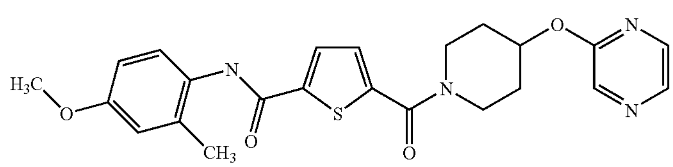 | B |
| 42 | 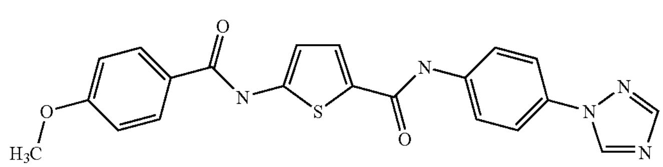 | B |
| 43 | 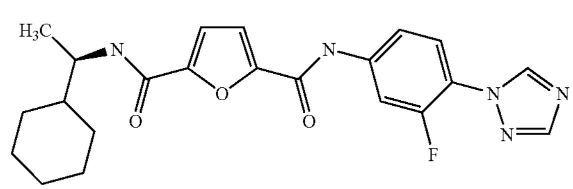 | B |

TABLE 1-continued

Representative Compounds of the Invention

| Compound Number | STRUCTURE | IC$_{50}$ |
|---|---|---|
| 44 | 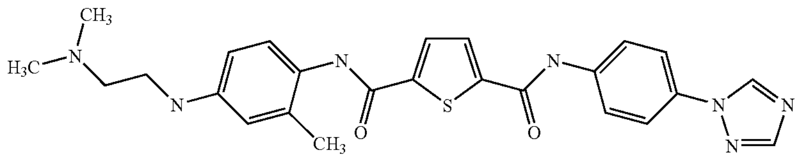 | B |
| 45 | 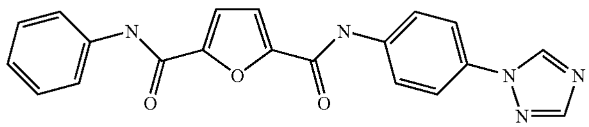 | B |
| 46 | 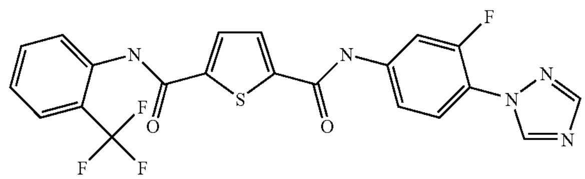 | B |
| 47 | 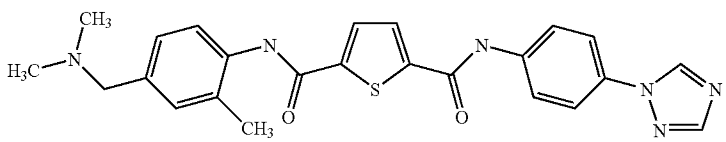 | B |
| 48 | 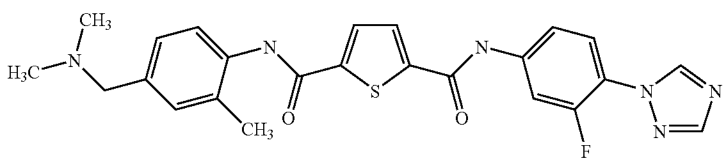 | B |
| 49 | 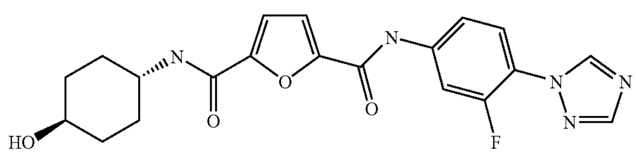 | B |
| 50 | 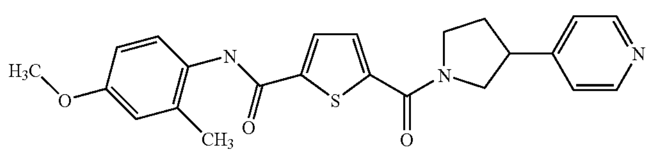 | B |
| 51 | 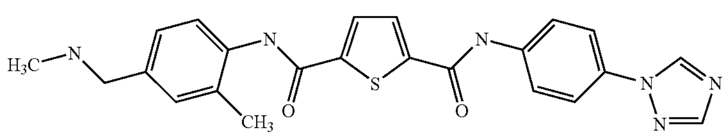 | B |
| 52 | 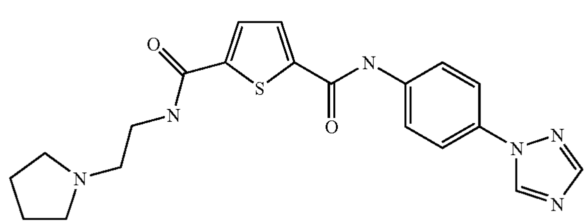 | B |

TABLE 1-continued

Representative Compounds of the Invention

| Compound Number | STRUCTURE | IC$_{50}$ |
|---|---|---|
| 53 | 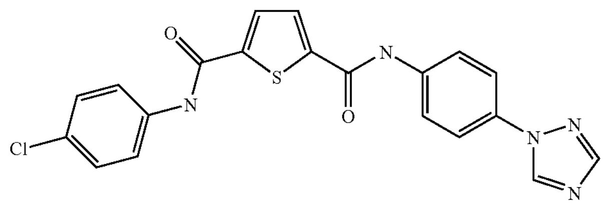 | B |
| 54 | 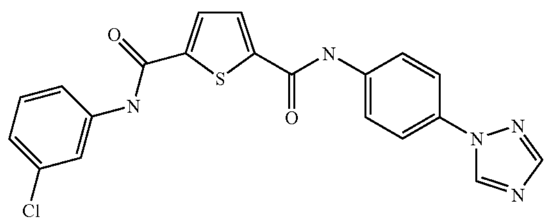 | B |
| 55 | 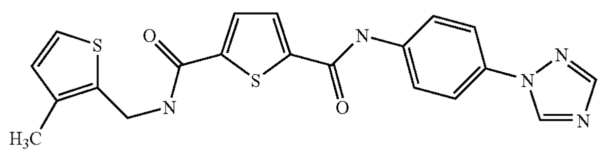 | B |
| 56 | 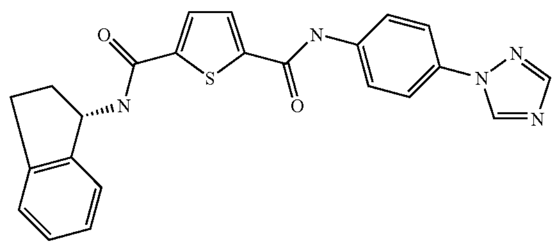 | B |
| 57 | 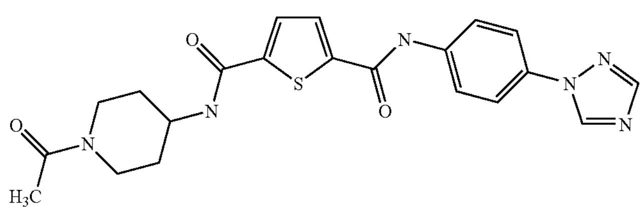 | B |
| 58 | 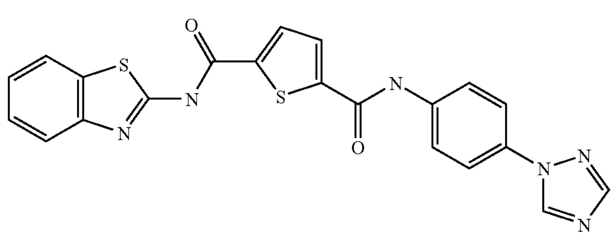 | B |
| 59 | 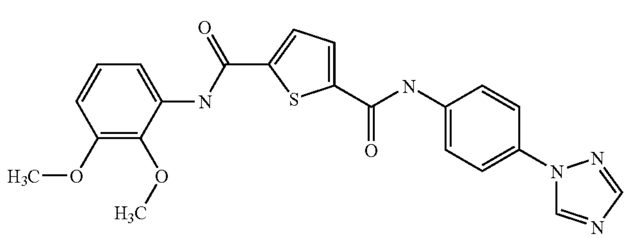 | B |

TABLE 1-continued

Representative Compounds of the Invention

| Compound Number | STRUCTURE | IC$_{50}$ |
|---|---|---|
| 60 | | B |
| 61 | | B |
| 62 | | B |
| 63 | | B |
| 64 | | B |
| 65 | | B |

TABLE 1-continued

Representative Compounds of the Invention

| Compound Number | STRUCTURE | IC$_{50}$ |
|---|---|---|
| 66 | 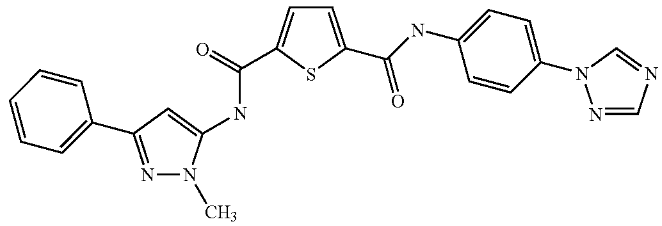 | B |
| 67 | 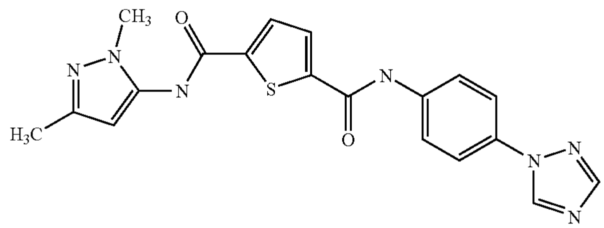 | B |
| 68 | 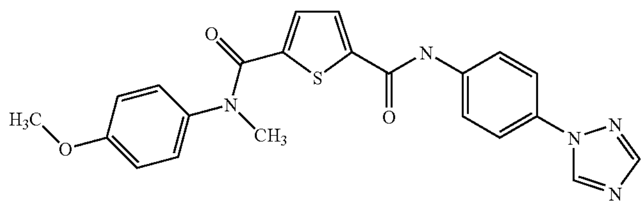 | B |
| 69 | 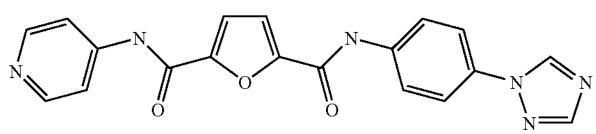 | B |
| 70 | 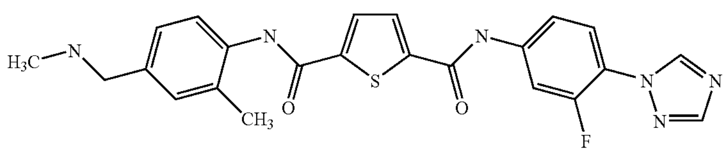 | B |
| 71 | 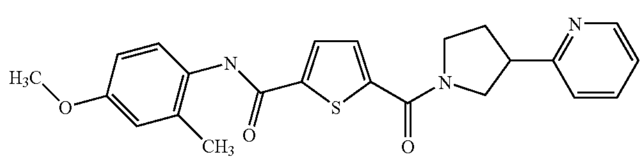 | B |
| 72 | 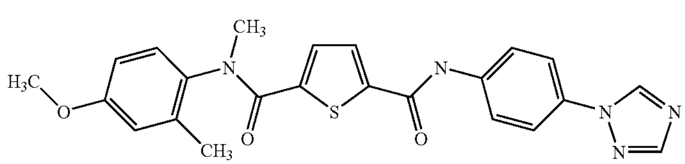 | B |
| 73 | 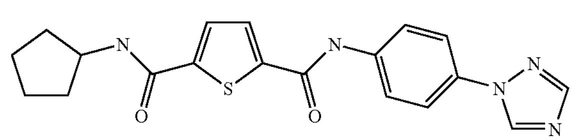 | B |

TABLE 1-continued

Representative Compounds of the Invention

| Compound Number | STRUCTURE | IC$_{50}$ |
|---|---|---|
| 74 | 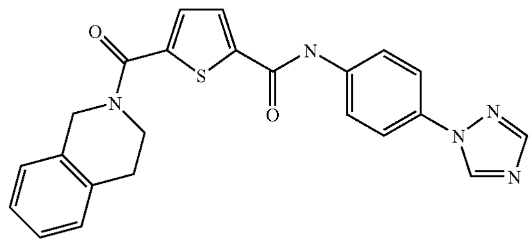 | B |
| 75 | 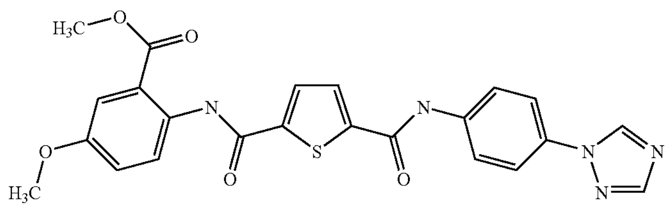 | B |
| 76 | 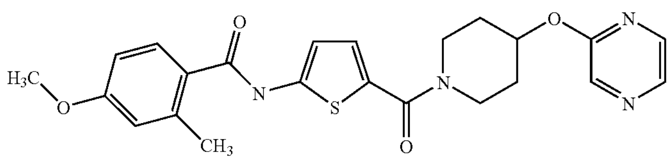 | B |
| 77 | 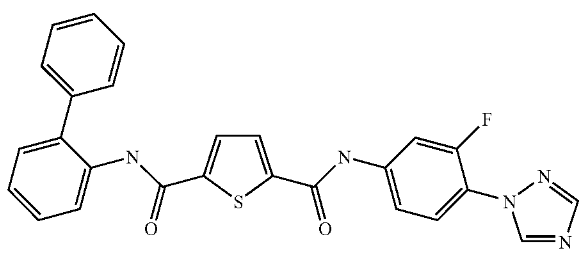 | B |
| 78 | 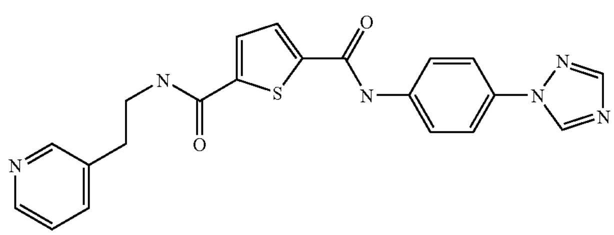 | B |
| 79 | 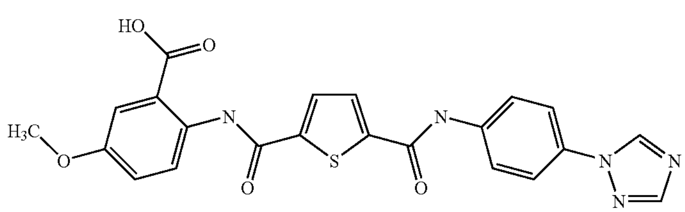 | B |
| 80 | 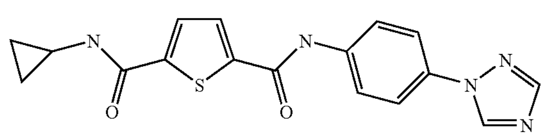 | C |

TABLE 1-continued

Representative Compounds of the Invention

| Compound Number | STRUCTURE | IC$_{50}$ |
|---|---|---|
| 81 | [structure: N-isopropyl thiophene-2,5-dicarboxamide with 4-(1,2,4-triazol-1-yl)phenyl] | C |
| 82 | [structure: N-cyclobutyl thiophene-2,5-dicarboxamide with 4-(1,2,4-triazol-1-yl)phenyl] | C |
| 83 | [structure: N-isobutyl thiophene-2,5-dicarboxamide with 4-(1,2,4-triazol-1-yl)phenyl] | C |
| 84 | [structure: piperidinyl thiophene-2,5-dicarboxamide with 4-(1,2,4-triazol-1-yl)phenyl] | C |
| 85 | [structure: morpholinyl thiophene-2,5-dicarboxamide with 4-(1,2,4-triazol-1-yl)phenyl] | C |
| 86 | [structure: N-butyl-N-methyl thiophene-2,5-dicarboxamide with 4-(1,2,4-triazol-1-yl)phenyl] | C |
| 87 | [structure: N-(2-dimethylaminoethyl) thiophene-2,5-dicarboxamide with 4-(1,2,4-triazol-1-yl)phenyl] | C |
| 88 | [structure: N-((S)-1-methoxypropan-2-yl) thiophene-2,5-dicarboxamide with 4-(1,2,4-triazol-1-yl)phenyl] | C |

//

TABLE 1-continued

Representative Compounds of the Invention

| Compound Number | STRUCTURE | IC$_{50}$ |
|---|---|---|
| 89 | 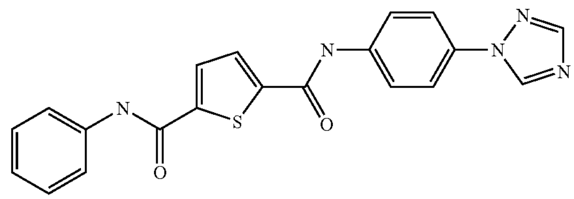 | C |
| 90 | 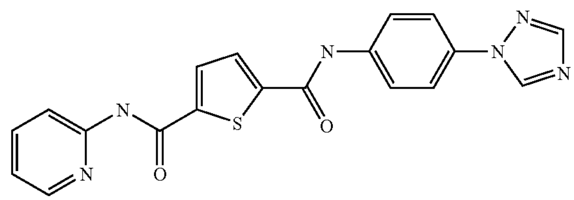 | C |
| 91 | 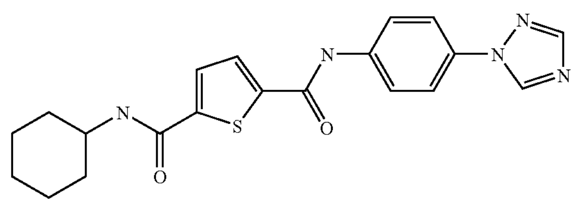 | C |
| 92 | 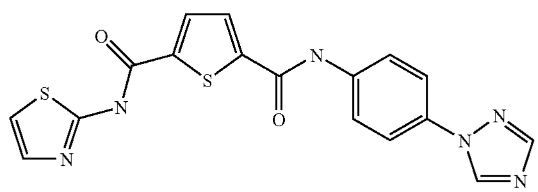 | C |
| 93 | 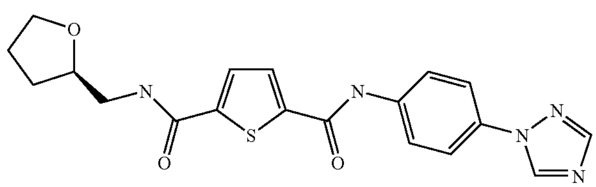 | C |
| 94 | 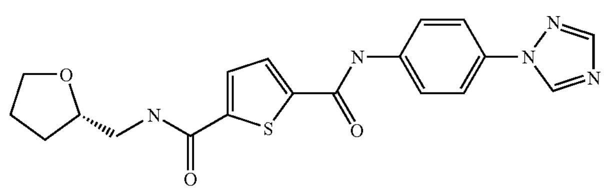 | C |
| 95 | 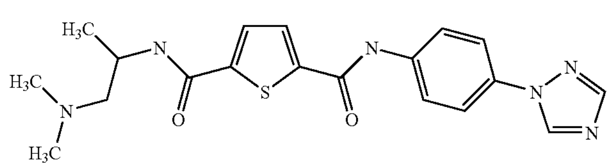 | C |
| 96 | 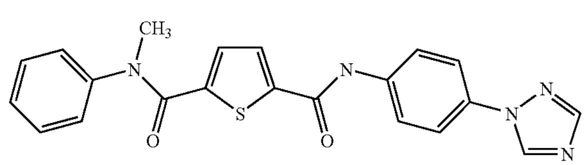 | C |

TABLE 1-continued

Representative Compounds of the Invention

| Compound Number | STRUCTURE | IC$_{50}$ |
|---|---|---|
| 97 | 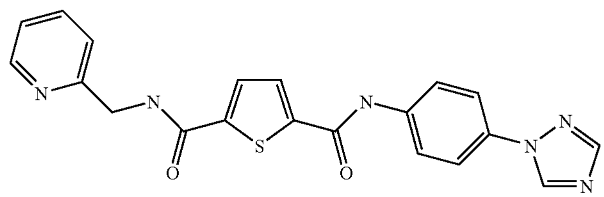 | C |
| 98 | 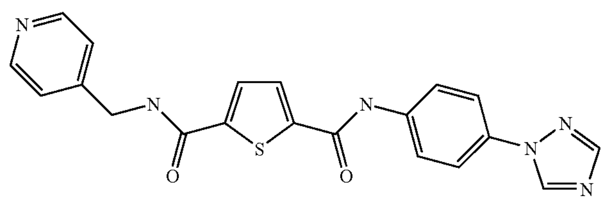 | C |
| 99 | 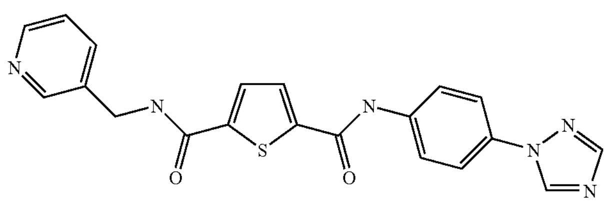 | C |
| 100 | 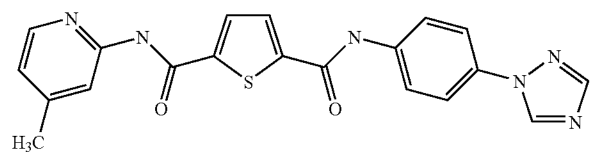 | C |
| 101 | 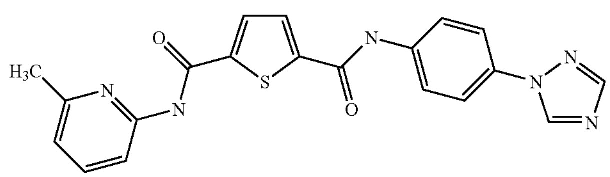 | C |
| 102 | 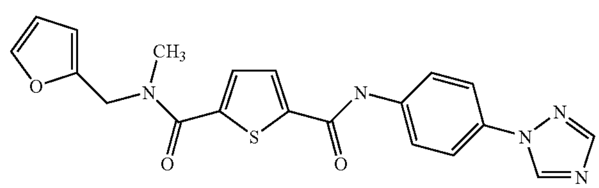 | C |
| 103 | 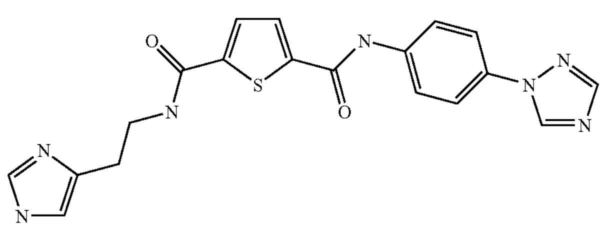 | C |
| 104 | 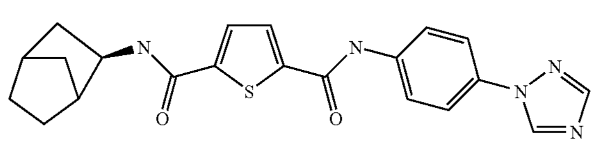 | C |

TABLE 1-continued
Representative Compounds of the Invention

| Compound Number | STRUCTURE | IC$_{50}$ |
| --- | --- | --- |
| 105 | 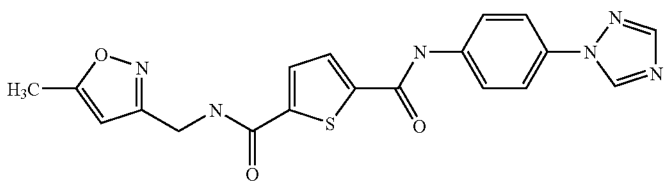 | C |
| 106 | 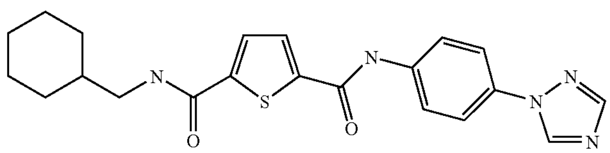 | C |
| 107 | 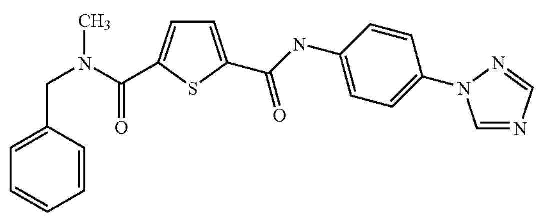 | C |
| 108 | 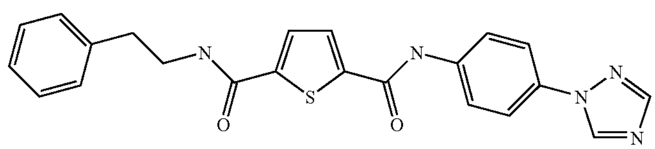 | C |
| 109 | 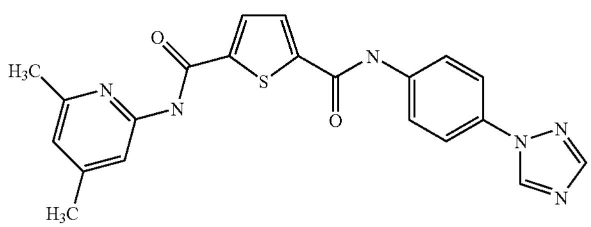 | C |
| 110 | 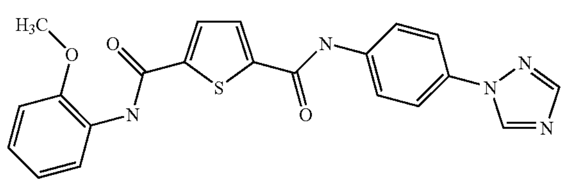 | C |
| 111 | 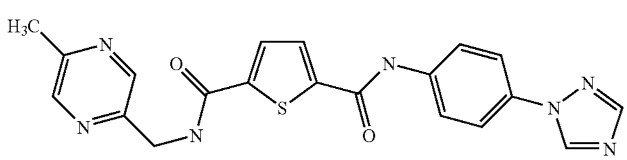 | C |
| 112 | 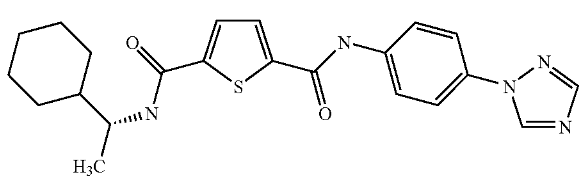 | C |

TABLE 1-continued

Representative Compounds of the Invention

| Compound Number | STRUCTURE | IC$_{50}$ |
|---|---|---|
| 113 | 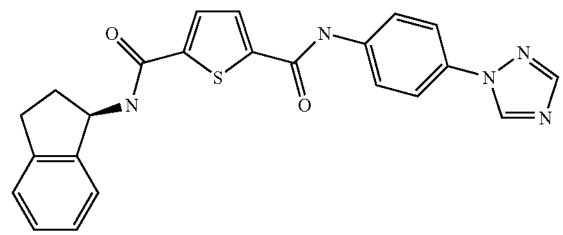 | C |
| 114 | 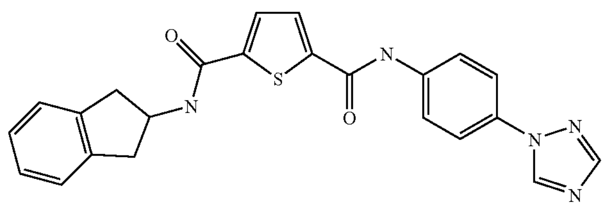 | C |
| 115 | 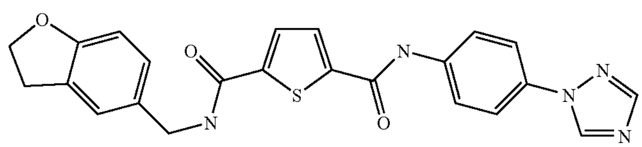 | C |
| 116 | 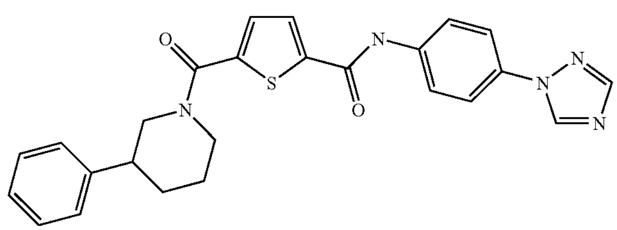 | C |
| 117 | 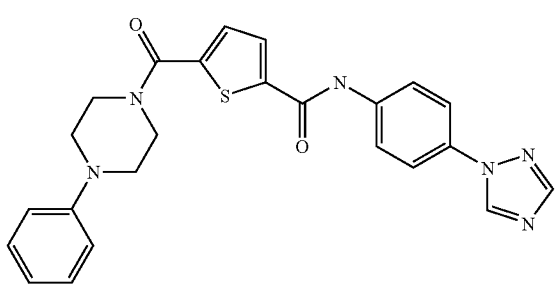 | C |
| 118 | 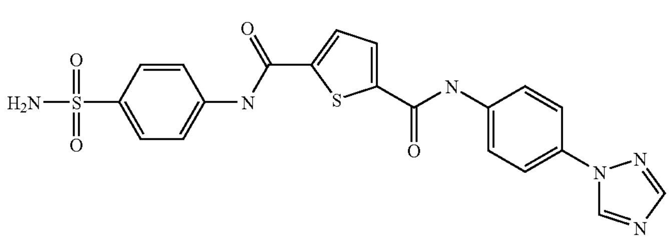 | C |

TABLE 1-continued

Representative Compounds of the Invention

| Compound Number | STRUCTURE | IC$_{50}$ |
|---|---|---|
| 119 | 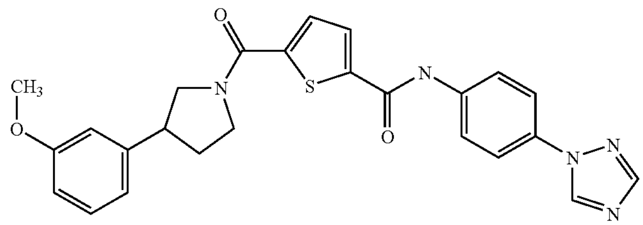 | C |
| 120 | 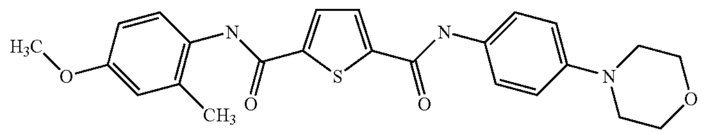 | C |
| 121 | 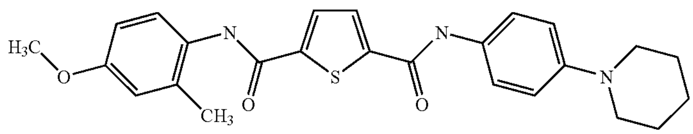 | C |
| 122 | 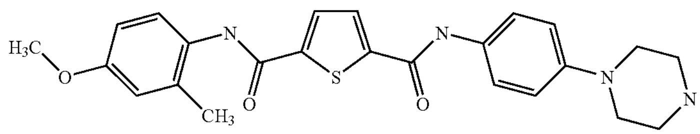 | C |
| 123 | 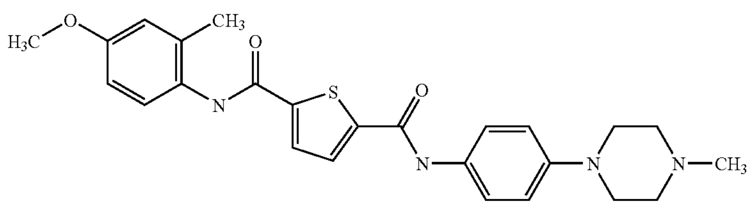 | C |
| 124 | 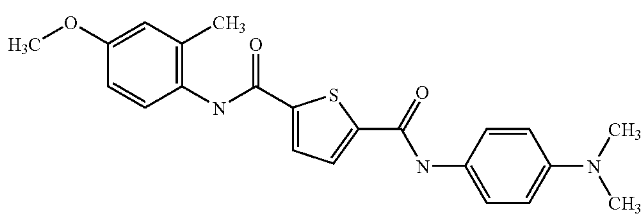 | C |
| 125 | 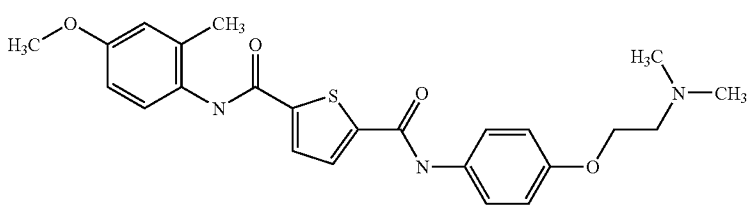 | C |
| 126 | 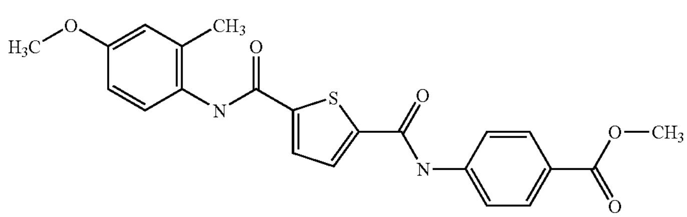 | C |

TABLE 1-continued

Representative Compounds of the Invention

| Compound Number | STRUCTURE | IC$_{50}$ |
|---|---|---|
| 127 | 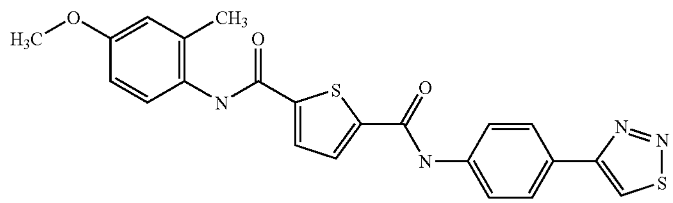 | C |
| 128 | 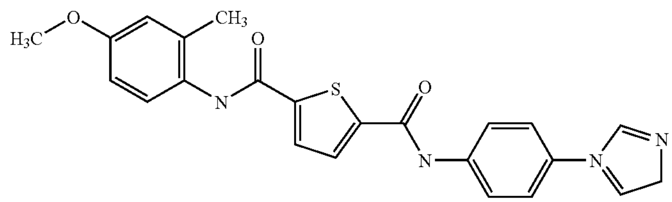 | C |
| 129 | 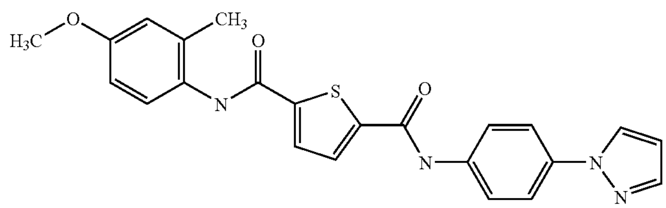 | C |
| 130 | 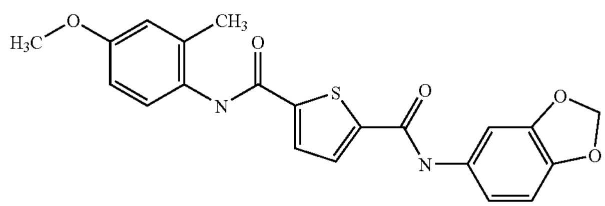 | C |
| 131 | 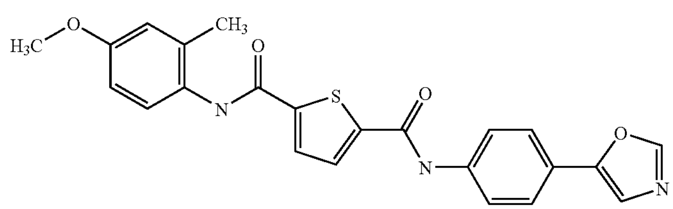 | C |
| 132 | 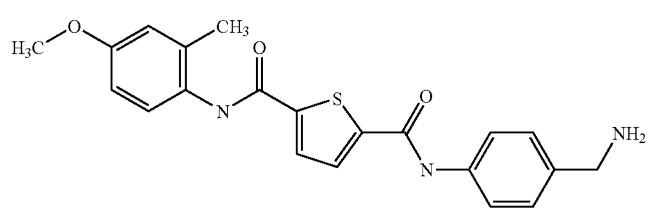 | C |
| 133 | 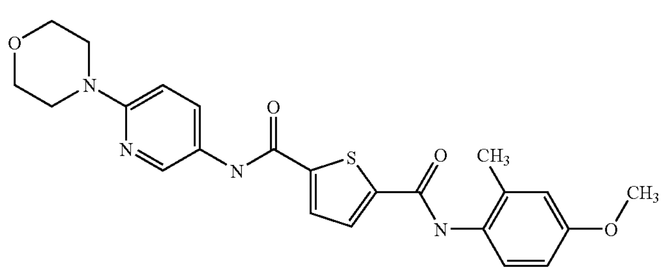 | C |

TABLE 1-continued

Representative Compounds of the Invention

| Compound Number | STRUCTURE | IC$_{50}$ |
|---|---|---|
| 134 | 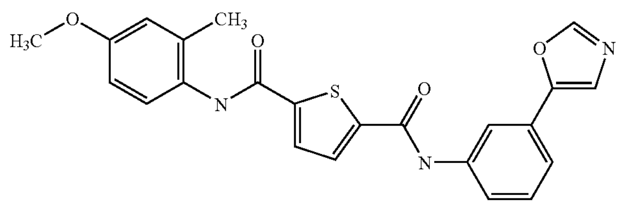 | C |
| 135 | 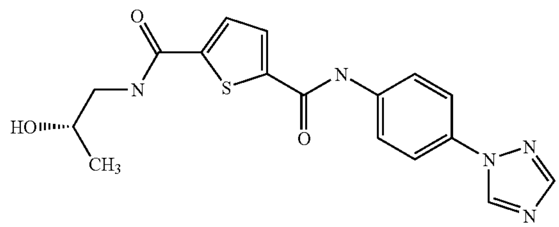 | C |
| 136 | 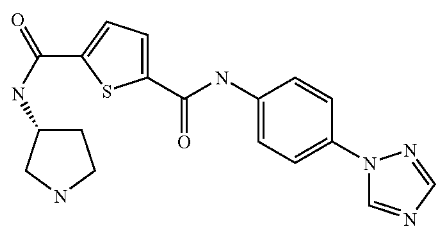 | C |
| 137 | 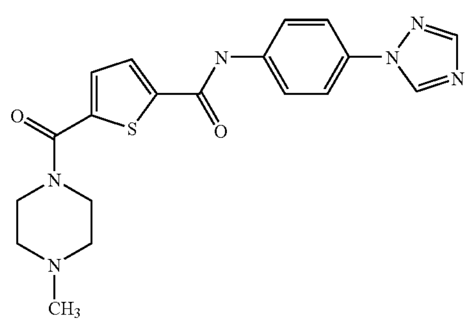 | C |
| 138 | 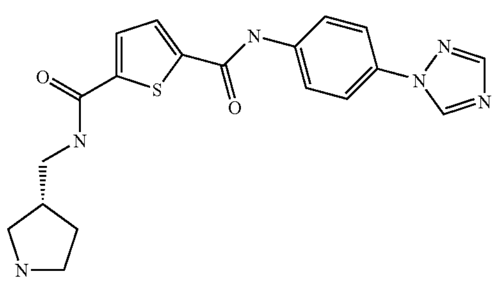 | C |
| 139 | 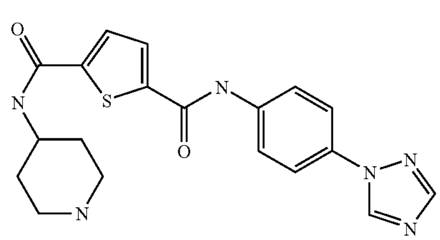 | C |

TABLE 1-continued

Representative Compounds of the Invention

| Compound Number | STRUCTURE | IC$_{50}$ |
|---|---|---|
| 140 | 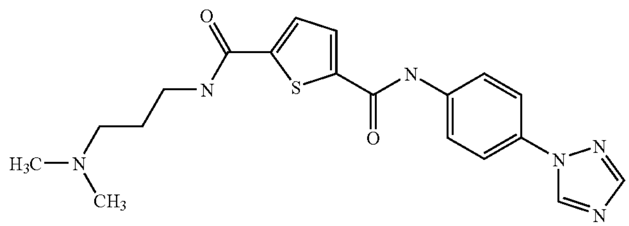 | C |
| 141 | 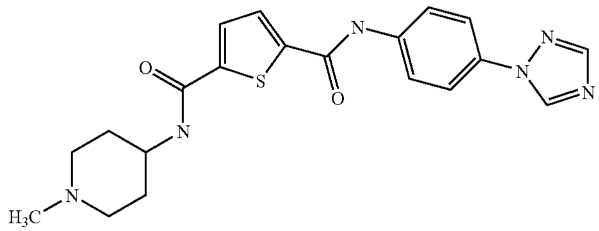 | C |
| 142 | 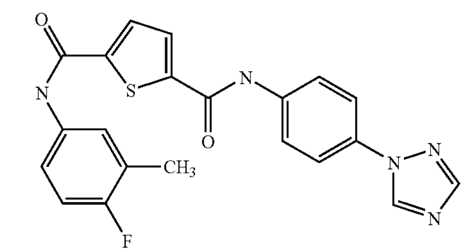 | C |
| 143 | 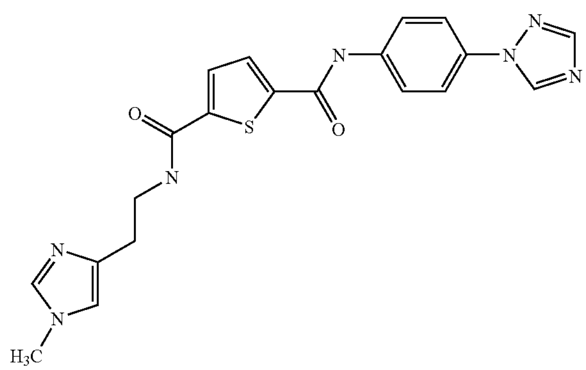 | C |
| 144 | 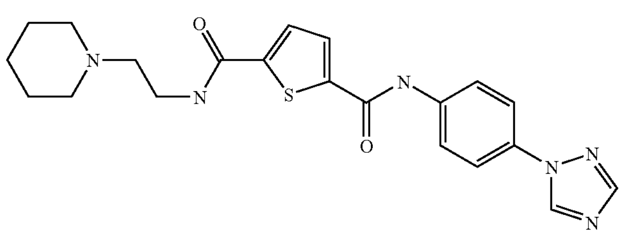 | C |
| 145 | 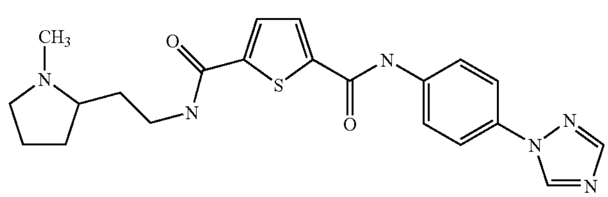 | C |

TABLE 1-continued

Representative Compounds of the Invention

| Compound Number | STRUCTURE | IC$_{50}$ |
|---|---|---|
| 146 | | C |
| 147 | | C |
| 148 | | C |
| 149 | | C |
| 150 | | C |
| 151 | | C |

TABLE 1-continued

Representative Compounds of the Invention

| Compound Number | STRUCTURE | IC$_{50}$ |
|---|---|---|
| 152 | 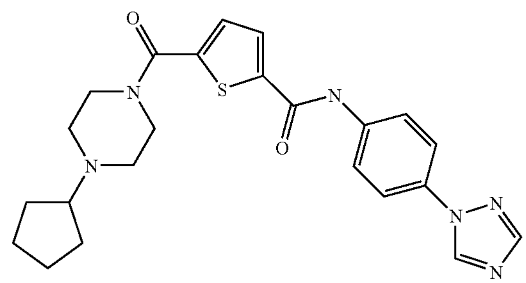 | C |
| 153 | 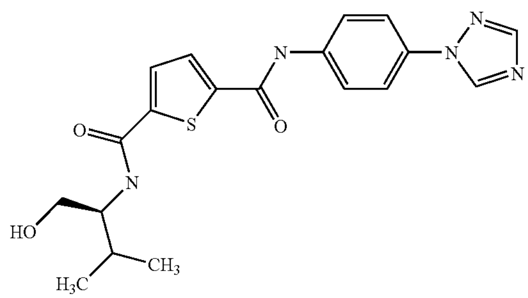 | C |
| 154 | 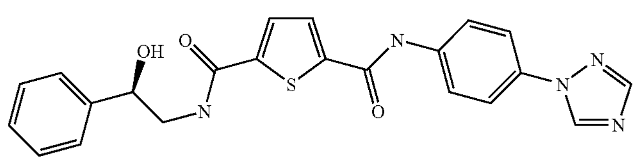 | C |
| 155 | 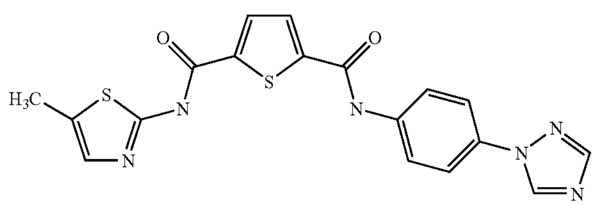 | C |
| 156 | 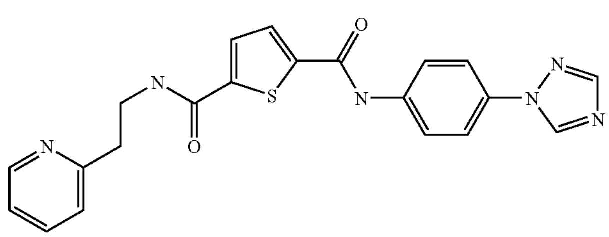 | C |
| 157 | 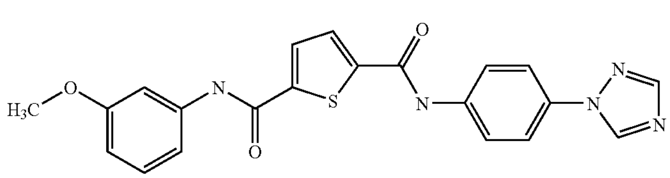 | C |

TABLE 1-continued

Representative Compounds of the Invention

| Compound Number | STRUCTURE | IC$_{50}$ |
|---|---|---|
| 158 | 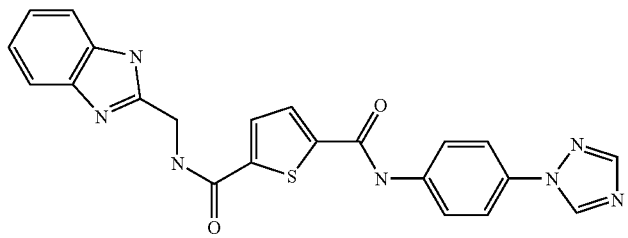 | C |
| 159 | 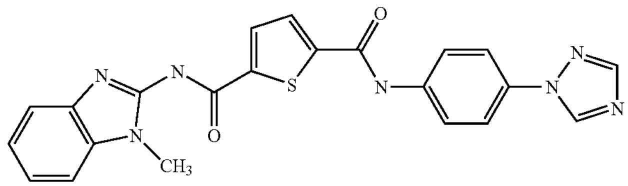 | C |
| 160 | 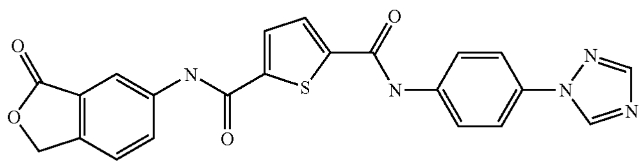 | C |
| 161 | 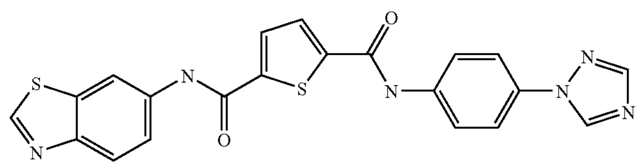 | C |
| 162 | 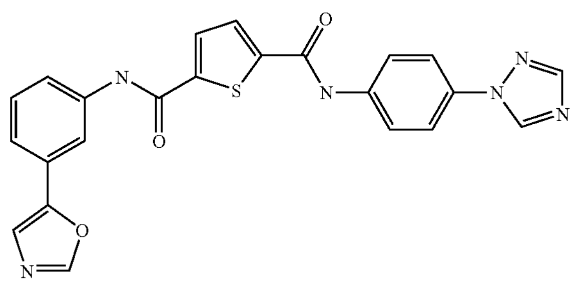 | C |
| 163 | 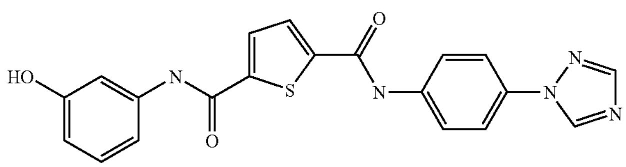 | C |
| 164 | 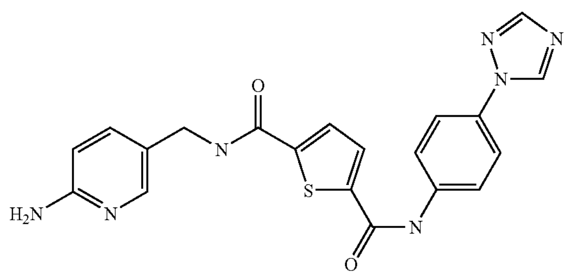 | C |

TABLE 1-continued

Representative Compounds of the Invention

| Compound Number | STRUCTURE | IC$_{50}$ |
|---|---|---|
| 165 | 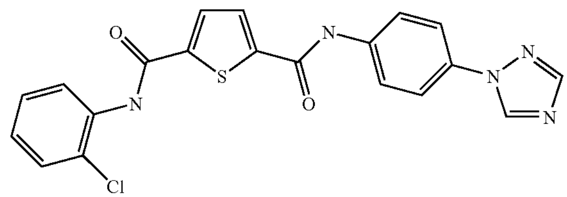 | C |
| 166 | 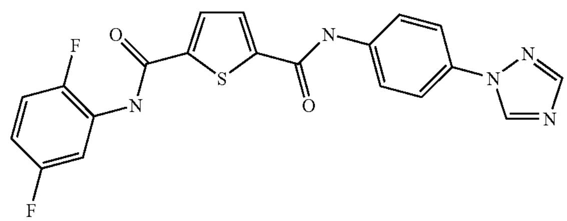 | C |
| 167 | 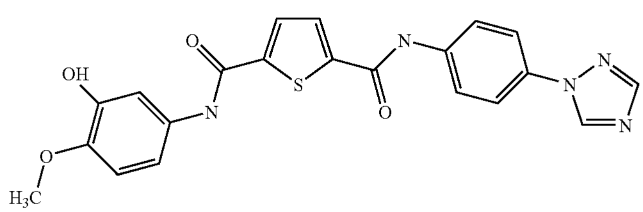 | C |
| 168 | 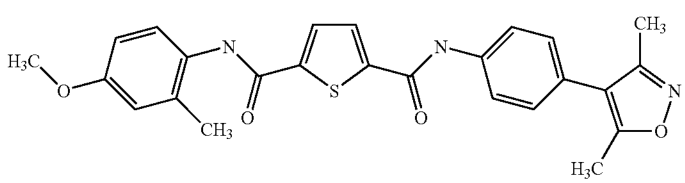 | C |
| 169 | 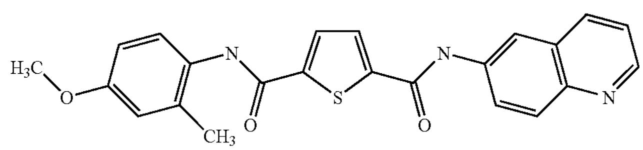 | C |
| 170 | 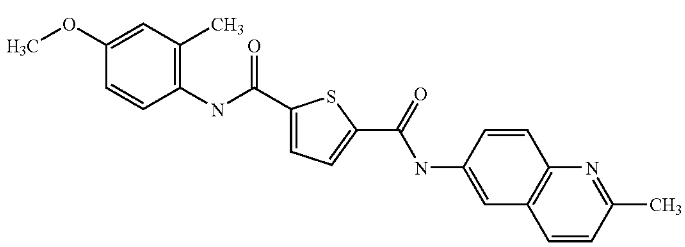 | C |
| 171 | 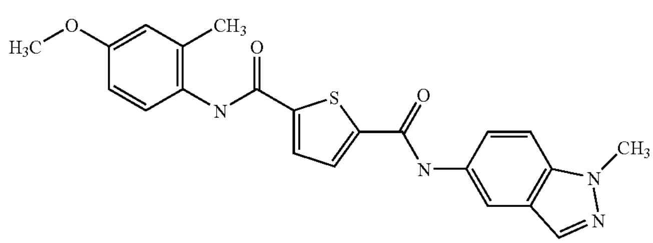 | C |

TABLE 1-continued

Representative Compounds of the Invention

| Compound Number | STRUCTURE | IC$_{50}$ |
|---|---|---|
| 172 | (structure) | C |
| 173 | (structure) | C |
| 174 | (structure) | C |
| 175 | (structure) | C |
| 176 | (structure) | C |
| 177 | (structure) | C |

TABLE 1-continued

Representative Compounds of the Invention

| Compound Number | STRUCTURE | IC$_{50}$ |
|---|---|---|
| 178 | 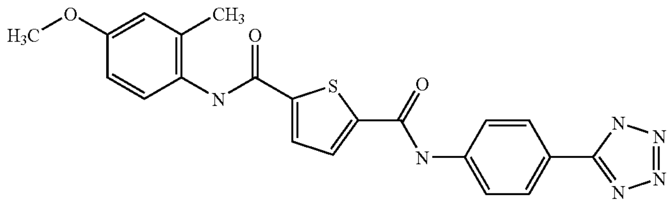 | C |
| 179 | 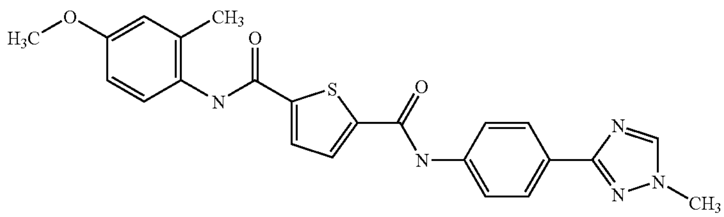 | C |
| 180 | 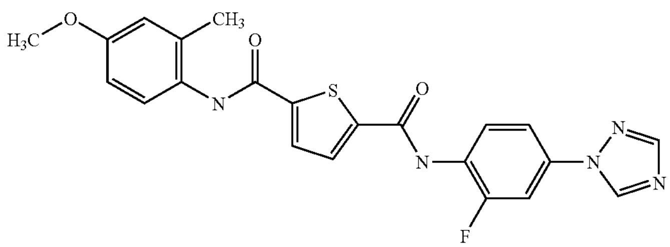 | C |
| 181 | 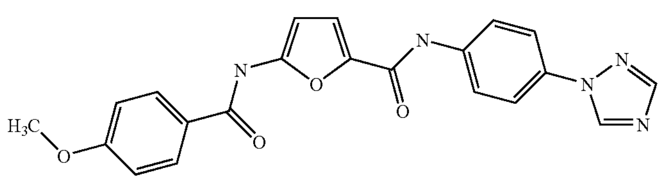 | C |
| 182 | 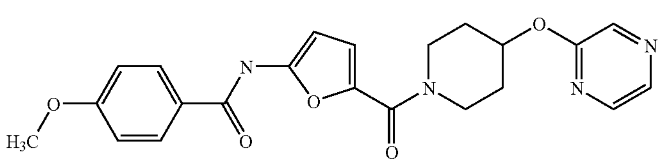 | C |
| 183 | 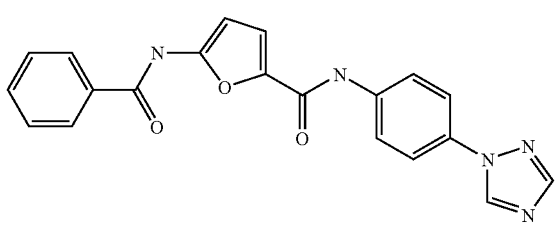 | C |
| 184 | 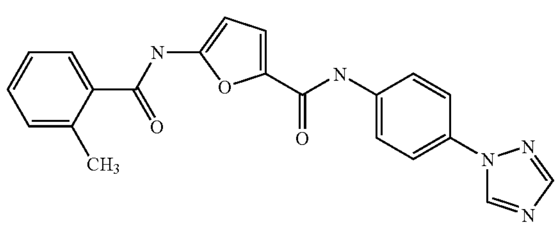 | C |

TABLE 1-continued

Representative Compounds of the Invention

| Compound Number | STRUCTURE | IC$_{50}$ |
|---|---|---|
| 185 | 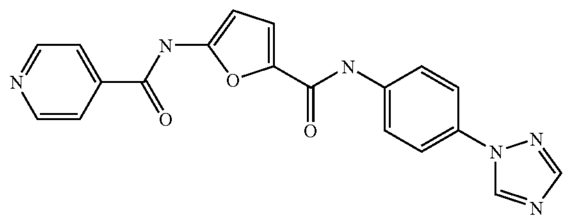 | C |
| 186 | 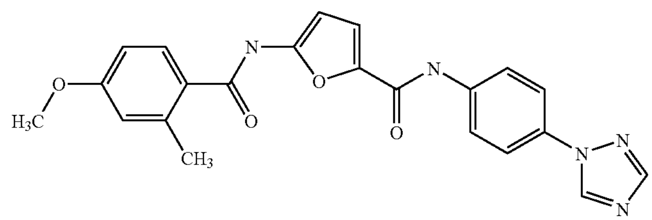 | C |
| 187 | 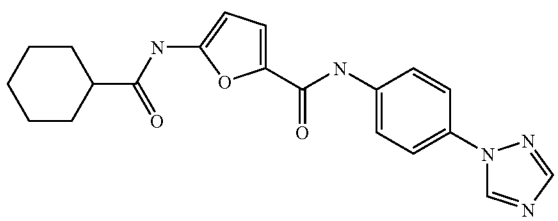 | C |
| 188 | 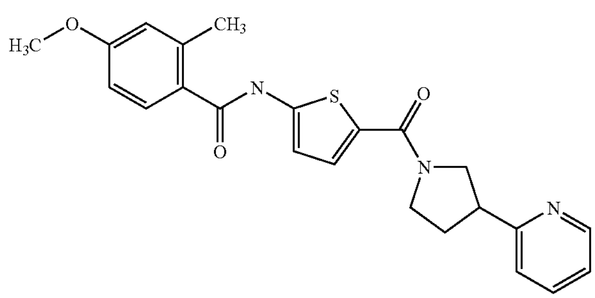 | C |
| 189 | 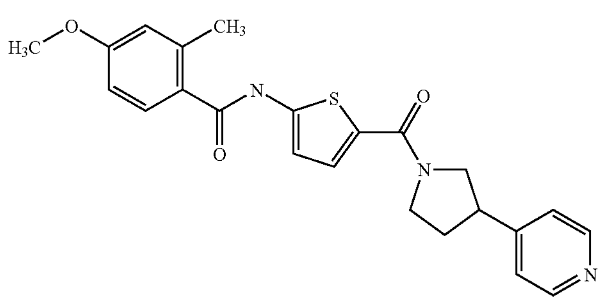 | C |
| 190 | 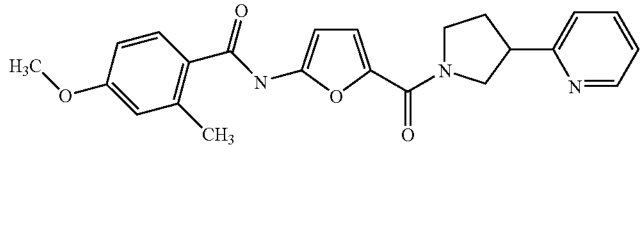 | C |

TABLE 1-continued

Representative Compounds of the Invention

| Compound Number | STRUCTURE | IC$_{50}$ |
|---|---|---|
| 191 | 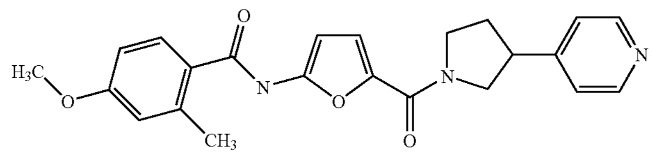 | C |
| 192 | 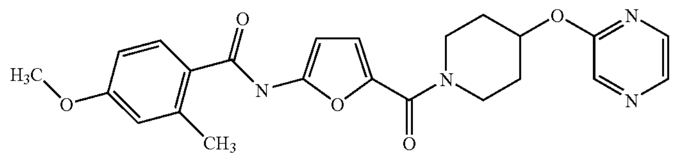 | C |
| 193 | 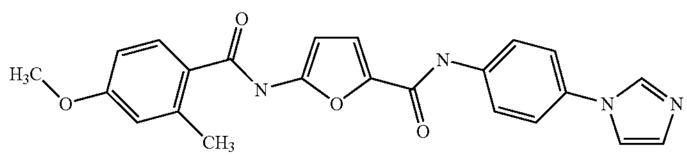 | C |
| 194 | 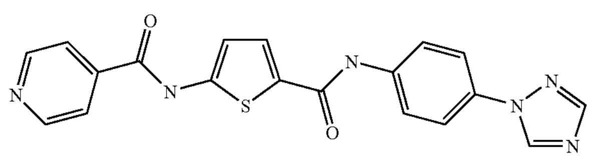 | C |
| 195 | 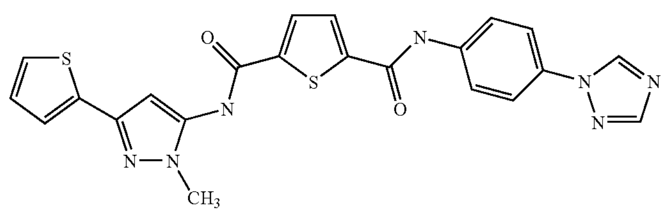 | C |
| 196 | 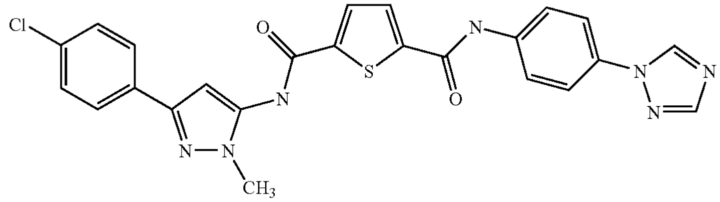 | C |
| 197 | 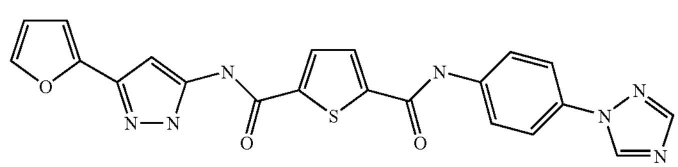 | C |
| 198 | 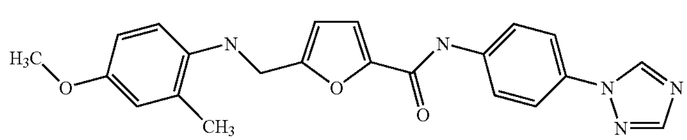 | C |

TABLE 1-continued

Representative Compounds of the Invention

| Compound Number | STRUCTURE | IC$_{50}$ |
|---|---|---|
| 199 | 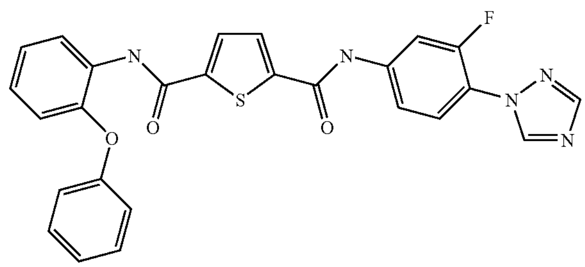 | C |
| 200 | 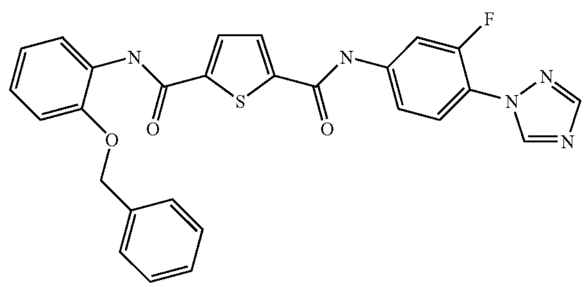 | C |
| 201 | 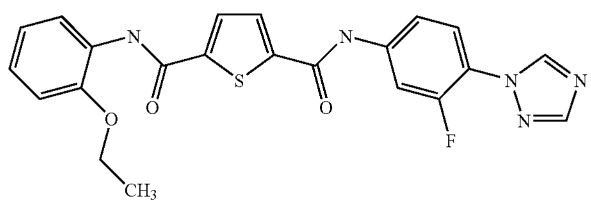 | C |
| 202 | 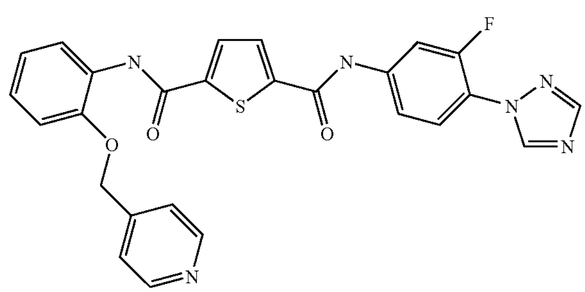 | C |
| 203 | 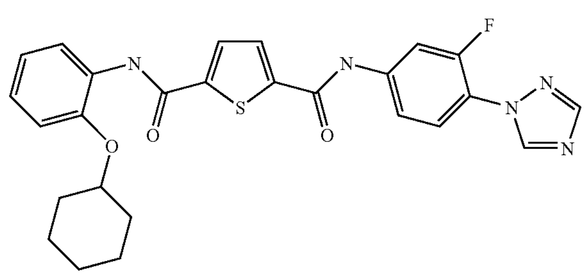 | C |

TABLE 1-continued

Representative Compounds of the Invention

| Compound Number | STRUCTURE | IC$_{50}$ |
|---|---|---|
| 204 | 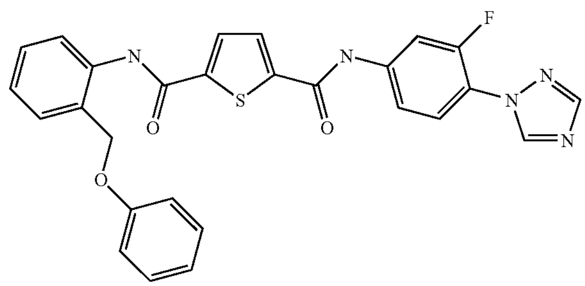 | C |
| 205 | 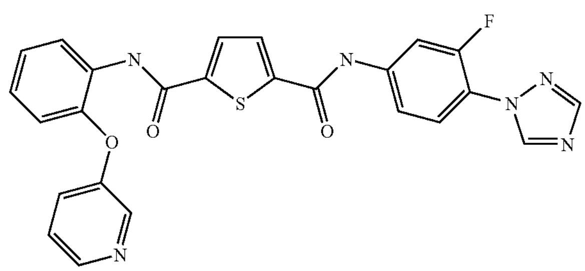 | C |
| 206 | 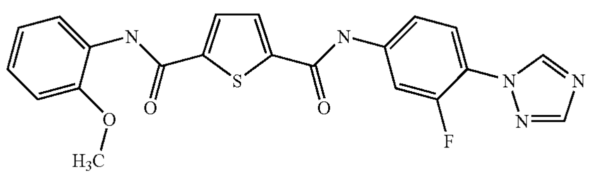 | C |
| 207 | 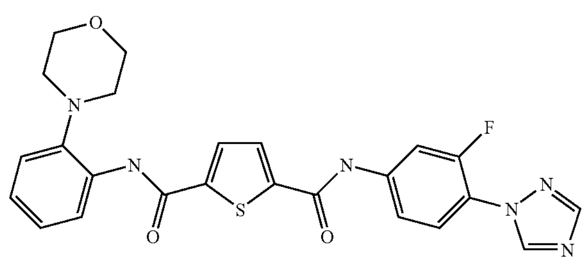 | C |
| 208 | 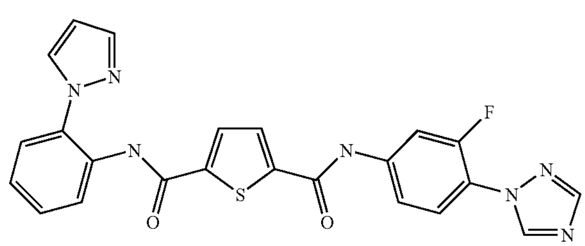 | C |

TABLE 1-continued
Representative Compounds of the Invention
| Compound Number | STRUCTURE | IC$_{50}$ |
|---|---|---|
| 209 | 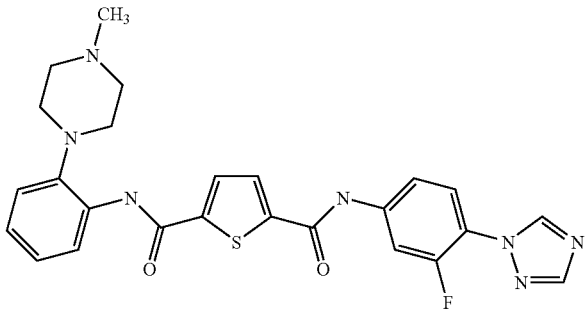 | C |
| 210 | 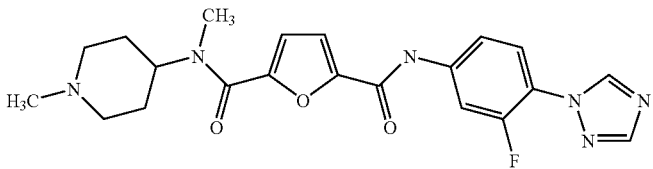 | C |
| 211 | 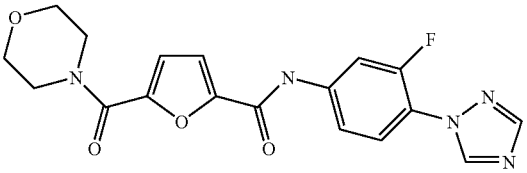 | C |
| 212 | 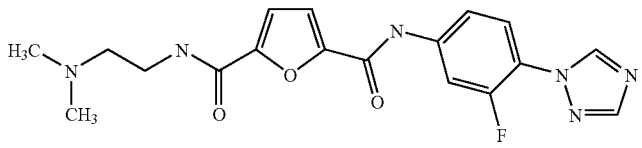 | C |
| 213 | 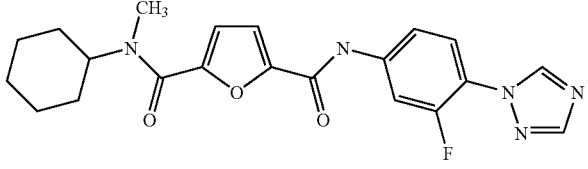 | C |
| 214 | 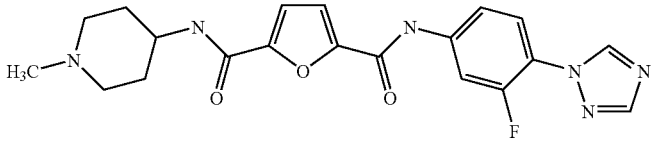 | C |
| 215 | 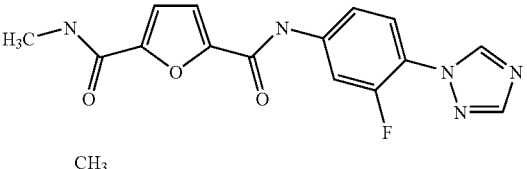 | C |
| 216 | 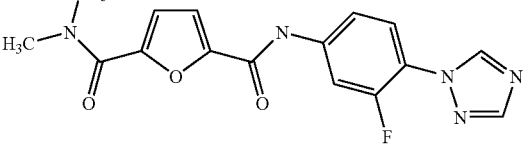 | C |

C. Preparation of the Compounds

The compounds described herein can be obtained from commercial sources or synthesized by conventional methods as shown below using commercially available starting materials and reagents. For example, the compounds can be made using the chemical scheme provided below:

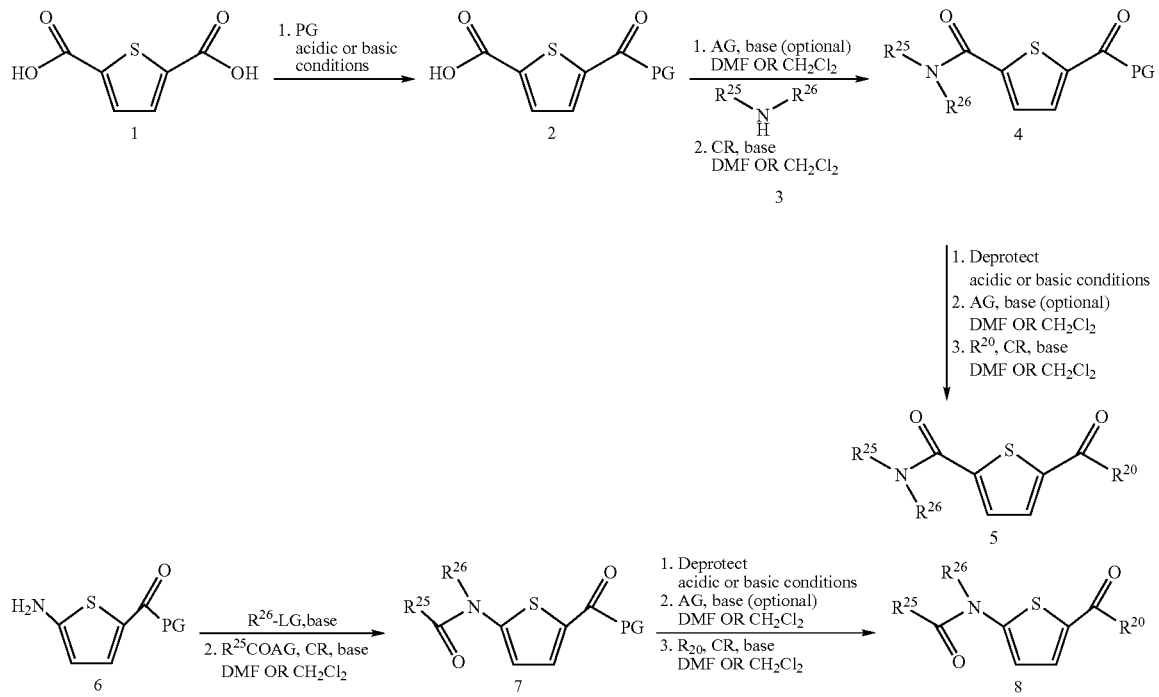

Where PG—Carboxyl protecting group such as silyl esters, alkyl esters, etc.
AG—Carboxyl activating group such as NHS, PFP, halide etc.
CR—Coupling reagent such as DCC, EDAC, DIEA
LG—leaving group Thiophene dicarboxylate 1, is selectively mono-protected using conventional carboxyl protecting groups to yield 2. The unprotected carboxyl group in 2 is then optionally activated by coupling with an activating agent and subsequently coupled with 3, to yield 4. 3 can be obtained commercially or by using conventional synthetic techniques known to one of ordinary skill in the art to make the desired $R^{25}$ and $R^{26}$ groups. 4 can be converted to 5 by deprotection of the carboxyl followed by coupling with $R^{20}$.

Aminothiophene 6, can be treated with a suitable electrophile $R^{26}$ in the presence of base followed by coupling with $R^{25}$ acyl derivative to yield 7. The protected carboxyl of 7 is deprotected and optionally activated and coupled with $R^{20}$ to yield 8.

The compounds described herein can be separated from a reaction mixture and further purified by a method such as column chromatography, high-pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds according to the invention have pharmacological properties; in particular, the compounds of Formula I can be inhibitors of protein kinases such as, for example, the inhibitors of the cyclin-dependent kinases, mitogen-activated protein kinase (MAPK/ERK), glycogen synthase kinase 3(GSK3beta) and the like. The cyclin dependent kinases (CDKs) include, for example, CDC2 (CDK1), CDK2, CDK4, CDK5, CDK6, CDK7 and CDK8. The novel compounds of Formula I are expected to be useful in the therapy of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease. Many of these diseases and disorders are listed in U.S. Pat. No. 6,413,974 cited earlier, the disclosure of which is incorporated herein.

More specifically, the compounds of Formula I can be useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of CDKs in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of Formula I can also be useful in the treatment of Alzheimer's disease, as suggested by the recent finding that CDK5 is involved in the phosphorylation of tau protein (J. Biochem, (1995) 117, 741-749).

Compounds of Formula I may induce or inhibit apoptosis. The apoptotic response is aberrant in a variety of human diseases. Compounds of Formula I, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of Formula I, as inhibitors of the CDKs, can modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of Formula I may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of Formula I may also be useful in inhibiting tumor angiogenesis and metastasis.

Compounds of Formula I may also act as inhibitors of other protein kinases, e.g., protein kinase C, her2, raf 1, MEK1, MAP kinase, EGF receptor, PDGF receptor, IGF receptor, PI3 kinase, weel kinase, Src, Abl and thus be effective in the treatment of diseases associated with other protein kinases.

Thus, another aspect of this invention is a method of treating a mammal (e.g., human) having a disease or condition associated with the CDKs by administering, a therapeutically effective amount of at least one compound of Formula I, or a pharmaceutically acceptable salt or solvate of said compound to the mammal.

The compounds of this invention may also be useful in combination with one or more of anti-cancer treatments such as radiation therapy, and/or one or more anti-cancer agents selected from the group consisting of cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™ (4-[2-[4-[(11R)-3,10-dibromo-8-chloro-6,11-dihydro-5H-benzo[5,6]cyclohepta[1,2-b]pyridin-11-yl-]-1-piperidinyl]-2-oxoehtyl]-1-piperidinecarboxamide, or SCH 66336 from Schering-Plough Corporation, Kenilworth, N.J.), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, cytoxan, and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a compound of Formula I and an additional therapeutic agent may be present in fixed amounts (dosage amounts) in a single dosage unit (e.g., a capsule, a tablet and the like). A commercial example of such single dosage unit containing fixed amounts of two different active compounds for oral administration is VYTORIN® (available from Merck Schering-Plough Pharmaceuticals, Kenilworth, N.J.).

If formulated as a fixed dose, such combination products employ the compounds of this invention within the dosage range described herein and the other pharmaceutically active agent or treatment within its dosage range. For example, the CDC2 inhibitor olomucine has been found to act synergistically with known cytotoxic agents in inducing apoptosis (*J. Cell Sci.*, (1995) 108, 2897. Compounds of Formula I may also be administered sequentially with known anticancer or cytotoxic agents when a combination formulation is inappropriate. The invention is not limited in the sequence of administration; compounds of Formula I may be administered either prior to or after administration of the known anticancer or cytotoxic agent. For example, the cytotoxic activity of the cyclin-dependent kinase inhibitor flavopiridol is affected by the sequence of administration with anticancer agents. *Cancer Research*, (1997) 57, 3375. Such techniques are within the skills of persons skilled in the art as well as attending physicians.

Accordingly, in an aspect, this invention includes combinations comprising an amount of at least one compound of Formula I, or a pharmaceutically acceptable salt or solvate thereof, and an amount of one or more anti-cancer treatments and anti-cancer agents listed above wherein the amounts of the compounds/treatments result in desired therapeutic effect.

The pharmacological properties of the compounds of this invention may be confirmed by a number of pharmacological assays. The exemplified pharmacological assays which are described later have been carried out with the compounds according to the invention and their salts.

This invention is also directed to pharmaceutical compositions which comprise at least one compound of Formula I, or a pharmaceutically acceptable salt or solvate of said compound and at least one pharmaceutically acceptable carrier.

D. Formulation of Pharmaceutical Compositions

The pharmaceutical compositions provided herein contain therapeutically effective amounts of one or more of the compounds provided herein that are useful in the prevention, treatment, or amelioration of one or more of the symptoms of diseases or disorders associated with CDK-2, in a pharmaceutically acceptable carrier. Diseases or disorders associated with CDK-2 include, but are not limited to, inflammatory diseases, neurodegenerative diseases, cancer and diabetes. Pharmaceutical carriers suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients.

The compositions contain one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., *Ansel Introduction to Pharmaceutical Dosage Forms, Fourth Edition* 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with CDK-2 activity or in which CDK-2 activity is implicated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds using in vitro and in vivo systems described herein and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with CDK-2 activity or in which CDK-2 activity is implicated, as described herein.

In one embodiment, a therapeutically effective dosage should produce a serum concentration of active ingredient of from about 0.1 ng/ml to about 50-100 µg/ml. The pharmaceutical compositions, in another embodiment, should provide a dosage of from about 0.001 mg to about 2000 mg of compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

a. Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

b. Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

2. Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation. These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as transdermal patches, including iontophoretic and electrophoretic devices, and rectal administration, are also contemplated herein.

Transdermal patches, including iotophoretic and electrophoretic devices, are well known to those of skill in the art.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

6. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions.

In one embodiment, liposomal suspensions, including tissue-targeted liposomes, such as tumor-targeted liposomes, may also be suitable as pharmaceutically acceptable carriers. These may be prepared according to methods known to those skilled in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

7. Articles of Manufacture

The compounds or pharmaceutically acceptable derivatives may be packaged as articles of manufacture containing packaging material, a compound or pharmaceutically acceptable derivative thereof provided herein, which is effective for modulating the activity of CDK-2, or for treatment, prevention or amelioration of one or more symptoms of CDK-2 mediated diseases or disorders, or diseases or disorders in which CDK-2 activity, is implicated, within the packaging material, and a label that indicates that the compound or composition, or pharmaceutically acceptable derivative thereof, is used for modulating the activity of CDK-2, or for treatment, prevention or amelioration of one or more symptoms of CDK-2 mediated diseases or disorders, or diseases or disorders in which CDK-2 is implicated.

The articles of manufacture provided herein contain packaging materials. Packaging materials for use in packaging pharmaceutical products are well known to those of skill in the art. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which CDK-2 is implicated as a mediator or contributor to the symptoms or cause.

EXAMPLES

Example 1

Screening Method

Fluorescence Polarization Assay

The affinity of lead inhibitors binding to CDK-2 and CDK-2/cyclin A were determined by measuring a Ki value using a fluorescence polarization displacement assay. The deacetylated form of compound BMS-250595 was reacted with Alexa Fluor 647 to generate a compound (BMS-Alexa Fluor647) that bound to both proteins and provided a signal for fluorescence polarization displacement. Binding assays were performed in a 384 well Costar NBS coated plate. A total volume of 80 ml contained concentrations of CDK-2 or CDK-2/cyclin A at 2.2 mM and 0.22 mM, respectively. The concentration of BMS-Alexa Fluor647 was 50 nM. Serial dilutions of compounds were added to 12 wells. The final buffer concentration was 10 mM Hepes, pH 7.5, 150 mM NaCl, and 1 mM DTT. Samples were incubated at room temperature for 15 minutes and then read in an Analyst HT instrument using an excitation and emission wavelength of 580 and 680 nm, respectively. The displacement curves were analyzed by non-linear regression fitting to determine Ki values using the equations and Excel curve fitting tool described by Zhang et al., 2004 (Zhang R., Mayhood T., Lipari P., Wang Y., Durkin D., Syto R., Gesell J., McNemar C., and Windsor W., Analytical Biochemistry 331 (2004) 138-146)

Example 2

Confirmation Method

Isothermal Titration Calorimetry

Isothermal titration calorimetry (ITC) was used to obtain a full thermodynamic characterize of the binding affinity for several lead compounds. Human CDK-2 was dialyzed in to 10 mM Hepes, 150 mM NaCl, 10% glycerol, 1 mM DTT, pH 7.5 overnight with 2 changes of buffer. Both protein and ligand samples were prepared in 2 ml volumes. To prepare the ligand solution 20 ml of a 10 mM compound stock (in DMSO) was added to 2 ml of buffer. To match the DMSO concentration added to the ligand sample 20 ml of DMSO was also added to the 2 ml protein sample. The MicroCal MCS ITC (Northampton, Mass.) and included software were used for performing the titrations and analysis. The ITC runs were performed at 20° C. and mixed at a rate of 350 rpm. Injection volumes varied from 15-18 ml and 360 sec was recorded for each titration. When a clear baseline was not observed a blank titration was performed to subtract it from the raw data.

Example 3

Affinity Comparison Method

Temperature-Dependent Circular Dichroism

Often in drug discovery it is important to be able to rank order the affinity of lead inhibitors. One such method is Temperature-dependent Circular Dichroism (TdCD). When using inhibitor concentrations ~10-20 mM one can rank order and estimate the affinity of nanomolar to micromolar leads. TdCD is a method that induces protein unfolding by increasing the temperature of the protein sample and the increase in unfolded species is detected by measuring changes in the ellipticity in the far-UV which detects changes in secondary structure. The midpoint temperature of unfolding for the unliganded protein is referred to as Tm. Addition of inhibitors to the protein sample will increase the Tm because compounds bound to the protein stabilize the native state. The higher the affinity of a compound the higher the apparent Tm due to the requirement of increased energy to dissociate higher affinity compounds. The theoretical description for estimating the affinity of ligands from Tm values has been described in detail by Brandts and Lin (1990) (Brandts, J. F. and Lin, L-N, Biochemistry 1990 29, 6927-6940).

Three control compounds (BMS-250595, Purvalonal B, AG-12275) were analyzed by ITC and then characterized by the TdCD method. Using the Kd values obtained from ITC we were able to generate a standard curve relating Tm vs. Log ([Lfree]/Kd) for each compound, where [Lfree] is the concentration of unbound ligand at the Tm temperature. This standard curve is used to determine the Kd of compounds after the Tm value is measured by TdCD. The routine use of the TdCD method provides a relatively rapid analysis for estimating the affinity of lead compounds binding to proteins.

A 6 cell peltier temperature controlled Jasco 810 spectropolarimeter was used to measure temperature-dependent protein unfolding profiles. A 0.1 cm path length cell was used and the protein concentrations were 0.2 mg/ml (6 mM). The buffer was 10 mM Hepes, 150 mM NaCl, 10% glycerol, 1 mM DTT, pH 7.5. For TdCD measurements the wavelength was adjusted to 230 nm. A temperature rate of 1° C./min was used and an integration of 4 sec per sample at each temperature was recorded (every 0.5° C.). A band width of 4 nm was used to improve the signal to noise.

Example 4

Synthesis

General Experimental Notes

NMR spectra were acquired on a Mercury$_{plus}$ 400 MHz NMR Spectrometer (Varian) and are denoted in δ ppm. LC-MS data was obtained using an Agilent 1100 Series LC/IMSD (quadrupole, API-ES (Atmospheric Pressure Interface Electrospray)) with a capillary voltage set to 3500 V and running in positive mode.

Purification via reverse phase chromatography was accomplished using a C18 reverse phase column with a gradient of 0.1% trifluoroacetic acid in water to 95:5 acetonitrile:water at a flow rate of 20 mL/min. Samples were collected using a UV (Gilson, 254 nm) or mass spectra (Agilent 1100 Series LC/MSD model SL) signal.

Normal phase silica gel chromatography on a Biotage instrument was accomplished using a Quad UV System (P/N 07052) utilizing KP-SIL 32-63 um columns, 60 A with flash cartridges 12+M or 25+M.

Commonly Used Abbreviations
ACN Acetonitrile
AcOH Acetic acid
(Boc)$_2$O Di-tert-butyl-dicarbonate
CuTC Copper(I) thiophene-2-carboxylate
DCC Dicyclohexylcarbodiimide
DCU Dicyclohexylurea
DCM Dichloromethane
DIAD Diisopropylazodicarboxylate
DIEA Diisopropylethylamine
DMAP 4-Dimethylaminopyridine
DME Dimethoxyethane
DMF Dimethylformamide
DMFDMA N,N-Dimethylformamide dimethylacetal
DMSO Dimethyl sulfoxide
DPPF 1,1'-Bis(diphenylphosphino)ferrocene
EDCI (EDC) 1-(3-Dimethylaminopropyl)-3-ethylcarbodiimide hydrochloride
Et$_3$N Triethylamine
Et$_2$O Diethyl ether
EtOAc Ethyl acetate
EtOH Ethanol
h hour(s)
HATU N,N,N',N'-Tetramethyl-O-(7-Azabenzotriazol-1-yl) Uronium hexafluorophosphate
Hex Hexanes
HOBt 1-Hydrozybenzotriazole
HPLC High pressure liquid chromatography
LCMS Liquid chromatography mass spectrometry
LiBH$_4$ Lithium borohydride
LAH Lithium aluminum hydride
mCPBA meta-Chloroperoxybenzoic acid
MeOH Methanol
NaSMe Sodium methylsulfide
NMR Nuclear magnetic resonance
Pd$_2$(OAc) Palladium acetate
Pd$_2$(dba)$_3$ Tris(dibenzylideneacetone)dipalladium (0)
PdCl$_2$(dppf) [1,1'-Bis(diphenylphosphino)ferrocene]dichloropalladium(II), complex with DCM
Pd(PPh$_3$)$_2$Cl$_2$ Dichlorobis(triphenylphosphine)palladium (II)
PFP Pentafluorophenol
PMB p-methoxybenzyl
Pyr Pyridine
RT Room temperature
SiO$_2$ Silica gel
TFA Trifluoroacetic acid
THF Tetrahydrofuran
TLC Thin layer chromatography
TMS Trimethylsilyl
Zn(CN)$_2$ Zinc cyanide

Example 1

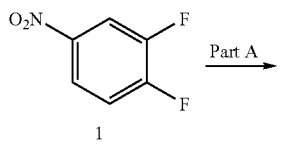

1

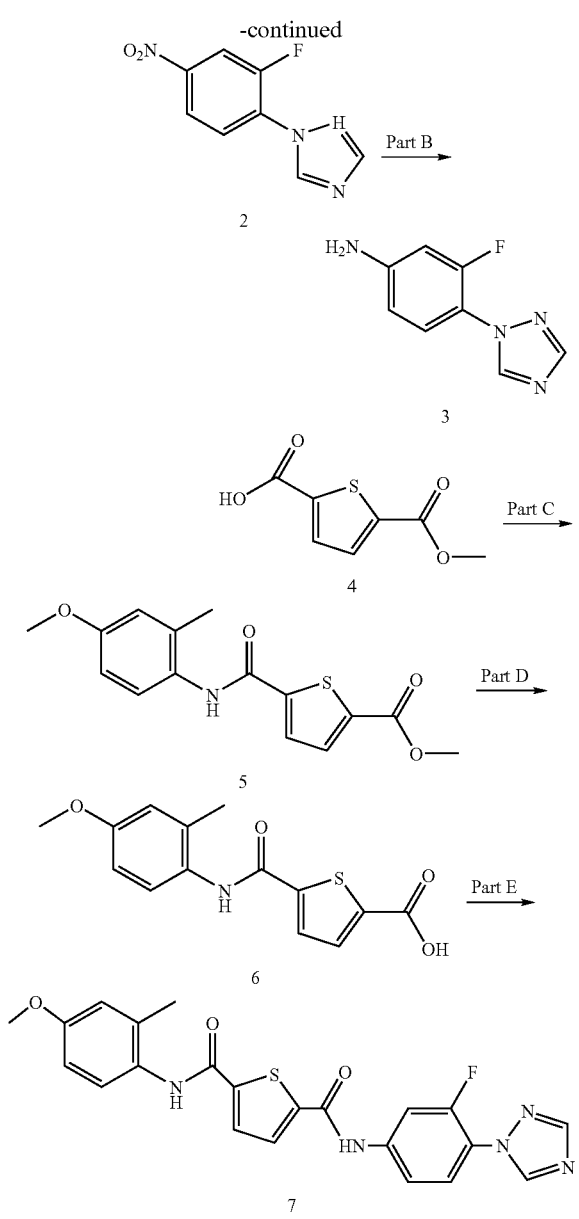

Part A

To a solution of 3,4-difluoronitrobenzene (318 mg, 2.0 mmol) in DMSO (4 mL), K$_2$HPO$_4$ (418 mg, 2.4 mmol) was added followed by 1,2,4-triazole (166 mg, 2.4 mmol). The resulting mixture was heated up to 90° C. and was stirred for 18 hours under argon. The reaction was cooled to room temperature and diluted by EtOAc (50 mL). The organic layer was washed by H$_2$O and brine, dried over Na$_2$SO$_4$, filtered and concentrated to give the crude product. The residue was purified by column chromatography (silica gel, Hexane/EtOAc=80:20) to give product 2 as white solid (320 mg, 77%). $^1$H NMR (400 MHz, DMSO-d$_6$): 9.18 (d, 1H), 8.50 (dd, 1H), 8.39 (s, 1H), 8.27 (m, 1H), 8.14 (dd, 1H). LC-MS m/z 209.1 (M+H).

Part B

Nitrobenzene 2 (320 mg, 1.54 mmol) was hydrogenated at 1 atm in the presence of 10% Pd/C (15 mg) in THF (20 mL) at room temperature overnight. After the reaction is completed, the reaction mixture was filtered through celite to remove the catalyst and was then concentrated under reduced pressure to give the crude product 3 (270 mg). LC-MS m/z 179.1 (M+H).

Part C

To a solution of monoacid 4 (1.86 g. 10 mmol) in DMF (10 mL) and HOBt (2.7 g, 20 mmol), EDC (2.0 mg, 10.5 mmol) was added. After the reaction mixture was stirred at room temperature for 10 min, 4-[1,2,4]triazol-1-yl-phenylamine (2.7 g, 20 mmol) was added. The resulting mixture was stirred at room temperature overnight and was poured into ice-water mixture (100 mL). The formed precipitate was then collected by filtration and was washed with saturated NaHCO$_3$, H$_2$O, 1 N HCl and H$_2$O. The resulted solid was dried under vacuum overnight to give the product 5 (2.7 g, 89%). $^1$H NMR (400 MHz, DMSO-d$_6$): 10.04 (s, 1H), 7.95 (d, 1H), 7.83 (d, 1H), 7.16 (d, 1H), 6.84 (d, 1H), 6.76 (dd, 1H), 3.84 (s, 3H), 3.73 (s, 3H), 2.18 (s, 3H).

Part D

A mixture of methyl ester 5 (2.7 g, 8.85 mmol) and 1 N LiOH (20 mL) in THF (40 mL) and MeOH (20 mL) was stirred for 3 hours at room temperature. After the solvent was removed under reduced pressure, the aqueous phase was diluted water (20 mL). 1 N HCl was then added to adjust the pH to about 3, and the formed precipitate was then collected by filtration. After washed with cold water, the solid was dried under vacuum overnight and product 6 was obtained as white solid (2.31 g, 90%). LC-MS m/z 292.1 (M+H).

Part E

To a solution of monoacid 6 (29 mg. 0.1 mmol) in DMF (5 mL), HOBt (27 mg, 0.2 mmol) and EDC (38 mg, 0.2 mmol) were added. After the reaction mixture was stirred at room temperature for 10 min, 3 (30 mg, 0.17 mmol) was added. The resulted mixture was stirred at room temperature overnight and was diluted with H$_2$O (20 mL). The formed precipitate was collected by filtration and washed with H$_2$O. The crude product 7 was purified by HPLC. LC-MS m/z 452.1 (M+H).

Example 2

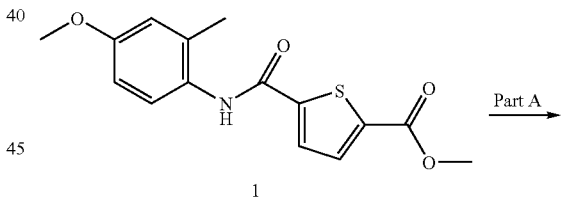

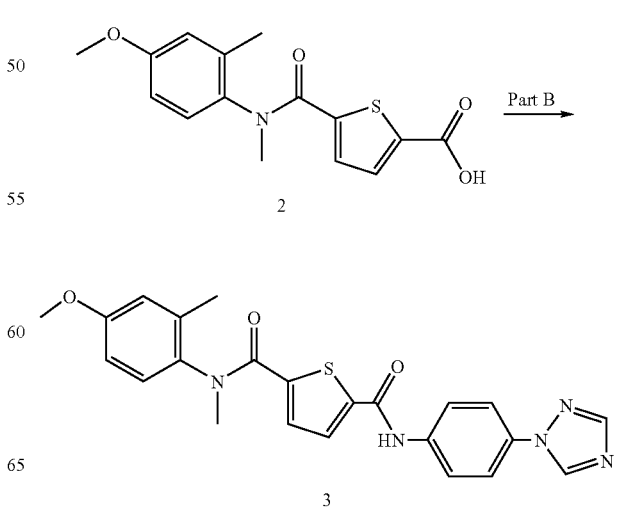

Part A

To a solution of 1 (60 mg, 0.2 mmol) in dry DMF (2 mL), NaH (40 mg, 60% in oil, 1 mmol) was added carefully. The resulted mixture was stirred at room temperature for 10 min and $CH_{3I}$ (280 mg, 2 mmol) was added. The resulted reaction mixture was heated up to 40° C. and stirred overnight. $H_2O$ (0.2 mL) was added to the mixture and the reaction was stirred for another 3 hour. After removing the solvent under reduced pressure, 1 N HCl (3 mL) was added to the residue. The formed precipitate was collected by filtration and was washed with $H_2O$, dried under vacuum overnight. The product 2 (41 mg, 68%) was obtained as white solid. LC-MS m/z 306.1 (M+H).

Part B

Compound 3 was synthesized with the same procedure as that described in Example 1, Part E. The crude product was purified by Prep-LC. LC-MS m/z 448.1 (M+H).

Example 3

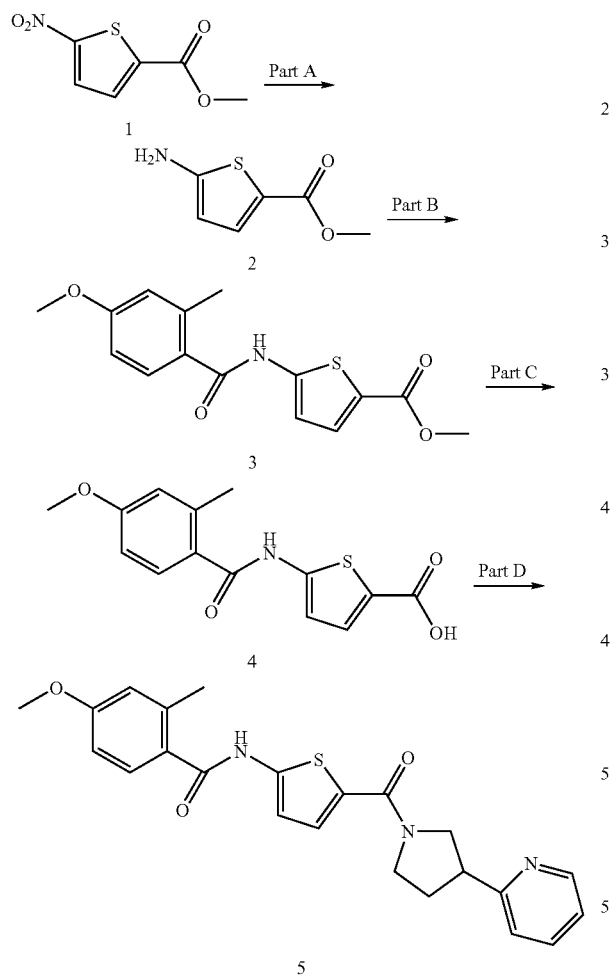

Part A

To a mixture of 2-nitrothiophene (600 mg, 3.2 mmol) and $SnCl_2·2H_2O$ (4.86 g, 25.6 mmol) in 95% EtOH (13.6 mL) was added concentrated HCl (13.6 mL) dropwise at room temperature (sufficient cooling was necessary to keep the reaction temperature under 35° C.). After the addition, the reaction mixture was stirred at 35° C. for 2 hours. EtOH was removed under vacuum and the aqueous layer was washed with hexane (50 mL×2). The pH of the aqueous layer was adjusted to pH-9 and was extracted three times with EtOAc (50 mL). The extracts were combined and dried over $Na_2SO_4$. After evaporation of solvent, the product was obtained as white solid (332 mg, 66%). $^1H$ NMR (400 MHz, DMSO-$d_6$): 7.15(d, 1H), 6.60(s, 2H), 5.10(d, 1H), 3.65(s, 3H). LC-MS m/z 158.1 (M+H).

Part B

To a solution of 2-methyl-4-methoxybenzonic acid (166 mg, 1 mmol) in DCM (5 mL) at RT, oxalyl chloride (0.15 mL) was added followed by the DMF (1 drop). The resulting mixture was stirred at RT for 3 hours and the solvent was evaporated under vacuum. To the flask with the residue of acetyl chloride, DCM (15 mL) was added, followed by 2 (100 mg, 0.64 mmol), pyridine (0.2 mL) and catalytical amount DMAP. The mixture was heated up to 40° C. and was stirred at this temperature for overnight. After cooling down to room temperature, EtOAc (80 mL) was added and the organic was washed with 1 N HCl, brine and dried over $Na_2SO_4$. After evaporation of solvent, the crude product 3 was used in the next step directly. LC-MS m/z 306.1 (M+H).

Part C

The compound 4 was synthesized with the same procedure as that described in Example 1, Part D. LC-MS m/z 292.1 (M+H).

Part D

The compound 5 was synthesized with the same procedure as that described in Example 1, Part E and purified by Prep-LC. LC-MS m/z 422.0 (M+H).

Example 4

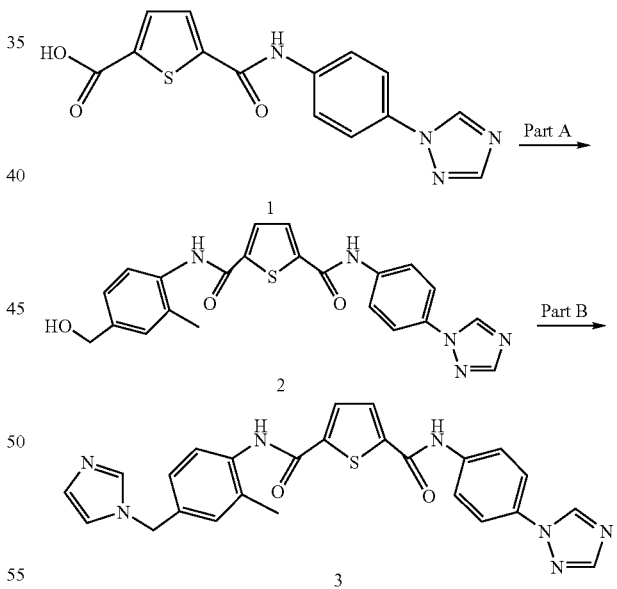

Part A

To a mixture of 1 (157, 0.5 mmol), HOBt (200 mg, 0.64 mmol) in DMF (5 ml) at 0° C. was added EDC (181 mg, 0.95 mmol) and the formed reaction mixture was stirred at 0° C. for 10 min. Then (4-amino-3-methyl-phenyl)-methanol (88 mg, 0.95 mmol) was added and the reaction mixture was first stirred at 0° C. for 0.5 hr and then at RT for overnight. To the reaction mixture, water was added and the formed precipitate was collected by filtration and was used directly in the next step after dried in the air. LC-MS m/z 434.1 (M+H).

Part B

At 0° C., the MsCl (26 uL, 0.33 mmol) was added into the mixture of 1 (143 mg, 0.33 mmol) and DIEA (115 uL, 0.66 mmol) in DMF (2 mL). The resulting mixture was stirred at 0° C. for 30 min and Cs₂CO₃ (326 mg, 1.0 mmol) was added to the reaction followed by imidazole (68 mg, 1.0 mmol). The mixture was stirred at room temperature overnight and diluted with EtOAc (30 mL) and the organic phase was washed with H₂O and brine. After concentration, the residue was purified by HPLC to give the product 2 as white solid. LC-MS m/z 484.1 (M+H).

Example 5

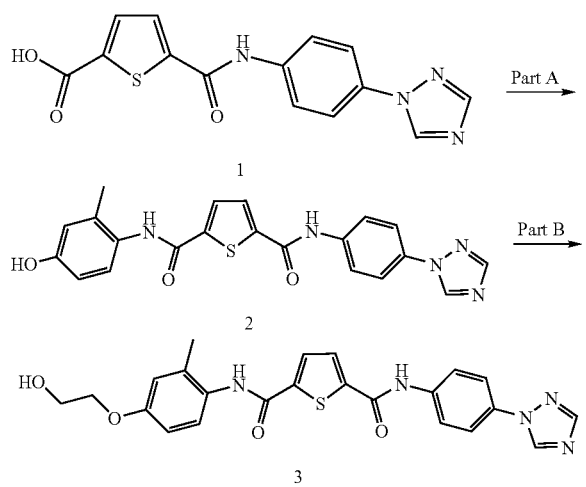

Part A

To a mixture of 1 (157 mg, 0.5 mmol), HOBt (200 mg, 0.64 mmol) in DMF (5 ml) at 0° C. was added EDC (181 mg, 0.95 mmol). After the formed reaction mixture was stirred at 0° C. for 10 min, 4-amino-3-methylphenol (117 mg, 0.95 mmol) was added and the reaction mixture was first stirred at 0° C. for 0.5 hr and then at RT for overnight. To the reaction mixture, water was added and the formed precipitate was collected by filtration and was used directly in the next step after dried in the air. LC-MS m/z 420.1 (M+H).

Part B

A mixture containing 2 (30 mg, 0.072 mmol), 2-bromoethanol (14 mg, 0.107 mmol) and Cs₂CO₃ (34 mg, 0.107 mmol) in DMF (2 ml) was stirred at 80° C. for overnight. To the reaction mixture, water (15 ml) was added and the mixture was extracted with ethyl acetate (3×15 ml). After evaporation of solvent, the residue was purified using Prep-HPLC to give the desired product. LC-MS m/z 464.1 (M+H).

Example 6

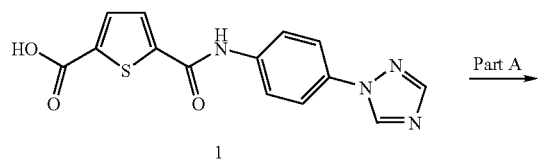

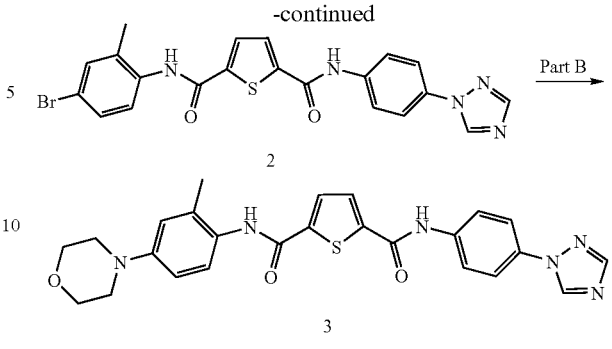

Part A

To a mixture of 1, HOBt (200 mg, 0.64 mmol) in DMF (5 ml) at 0° C. was added EDC (181 mg, 0.95 mmol) and the formed reaction mixture was stirred at 0° C. for 10 min. Then 4-Bromo-2-methyl-phenylamine (175 mg, 0.95 mmol) was added and the reaction mixture was first stirred at 0° C. for 0.5 hr and then at RT for overnight. To the reaction mixture, water was added and the formed precipitate was collected by filtration and was used directly in the next step after dried in the air. LC-MS m/z 467.1 (M+H).

Part B

A reaction mixture containing 2 (30 mg, 0.06 mmol), morpholine (8 mg, 0.09 mmol), Pd₂(dba)₃ (2 mg), biphenyl-3-yl-di-tert-butyl-phosphane (2 mg, 0.006 mmol) and sodium t-butoxide (12 mg, 0.012 mmol) in dioxane (2 mL) was degassed three times with Ar and was then heated under Ar at 90° C. for overnight. After cooled to RT, the reaction mixture was filtered through celite and was concentrated. The residue was then purified using prep-HPLC to give 8 mg of product. LC-MS m/z 489.2 (M+H).

Example 7

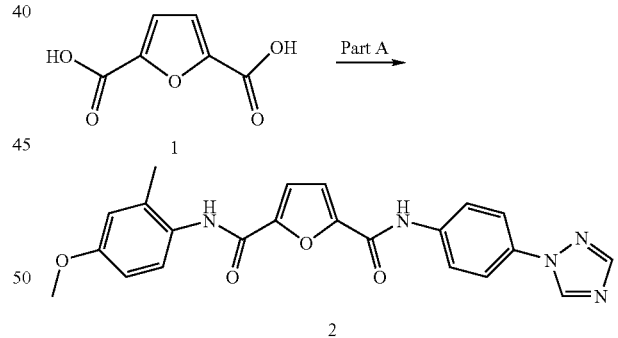

Part A

To a solution of 1 (80 mg, 0.5 mmol) in DMF (5 mL) at 0° C., HOBt (135 mg, 1.0 mmol) was added, followed by EDCI (191 mg, 1.0 mmol). After stirring at 0° C. for 0.5 h, 4-[1,2,4]triazol-1-yl-phenylamine (80 mg, 0.5 mmol) was added. 4-Methoxy-2-methyl-phenylamine (70 mg, 0.5 mmol) was added 10 min later. The reaction was then warmed up to RT and was stirred at this temperature for overnight. Water was added and the formed precipitated was collected by filtration, which was purified using prep-HPLC to give the desired product (30 mg). LC-MS m/z 418.2 (M+H).

All references cited herein, whether in print, electronic, computer readable storage media or other form, are expressly incorporated by reference in their entirety, including but not limited to, abstracts, articles, journals, publications, texts, treatises, internet web sites, databases, software packages, patents, and patent publications. A number of embodiments of the invention have been described. Nevertheless, it will be understood that various modifications may be made without departing from the spirit and scope of the invention. These modifications specifically include but are not limited to the addition of substituents to carbon or nitrogen atoms, or as otherwise appropriate, as envisioned by and described in the specification; the resulting molecules are within the spirit and scope of the invention. Accordingly, other embodiments are within the scope of the following claims and the Summary of the invention.

What is claimed is:

1. A compound of formula (I)

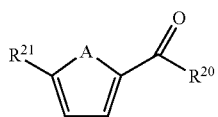

Formula I or a pharmaceutically acceptable salt or ester thereof, wherein
A is O or S;
$R^{20}$ is:

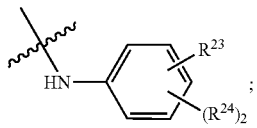

$R^{21}$ is —C(O)N($R^{25}R^{26}$);
$R^{23}$ is hydrogen, alkyl, alkoxy, alkoxyalkylamino, amino, alkylamino, dialkylamino, alkylheterocyclyl, alkylaryl, alkylheteroaryl, amido, aryl, alkoxyoxo, halo, heteroaryl, heterocyclyl, cyano, oxo, or aminoalkyl, wherein each of said alkyl, alkoxy, alkoxyalkylamino, amino, alkylamino, dialkylamino, alkylheterocyclyl, alkylaryl, alkylheteroaryl, aryl, alkoxyoxo, heteroaryl, heterocyclyl and aminoalkyl is either unsubstituted or optionally independently substituted with 1-3 independently selected $P^1$ susbtituents, where $P^1$ is alkyl, aryl, heteroaryl, heterocyclyl, cycloalkyl, alkoxy, amino, alkylamino, dialkylamino, or alkylthio, or two $P^1$ adjacent moieties together form an alkylenedioxy moiety fused to said aryl, heteroaryl, heterocyclyl ring they are attached to;
$R^{24}$ is hydrogen, halo, alkyl, alkylene, lower alkyl, aryl, heteroaryl, heterocyclyl, alkoxy, amino, aminoalkyl, alkylamino, dialkylamino, alkylthio, trihaloalkyl, wherein each of said alkyl, alkylene, lower alkyl, aryl, heteroaryl, heterocyclyl, alkoxy, amino, aminoalkyl, alkylamino, dialkylamino, alkylthio, trihaloalkyl is either unsubstituted or optionally independently substituted with 1-3 independently selected $P^1$susbtituents, where $P^1$ is alkyl, aryl, heteroaryl, heterocyclyl, cycloalkyl, alkoxy, amino, alkylamino, dialkylamino, or alkylthio; or two $R^{24}$ groups, which substitute atoms in a 1,2 or 1,3 arrangement on the phenyl ring said $R^{24}$ is shown attached to together form —O—(CH$_2$)$_y$—O—, —S—(CH$_2$)$_y$—O—, —S—(CH$_2$)$_y$—S, —CH═CH— CH═N—, —N═CH—CH═N—, or —S—CH═N— where y is 1 or 2;

or alternately $R^{23}$ and $R^{24}$ together form an aryl, heteroaryl or heterocyclyl ring with said aryl, heteroaryl or heterocyclyl ring being fused to the phenyl ring they are shown attached to;

and $R^{25}$ and $R^{26}$ are linked together to form a six-membered heterocyclyl or heteroaryl.

2. The compound of claim 1, wherein $R^{23}$ is hydrogen, alkyl, alkoxy, alkoxyalkylamino, amino, alkylamino, dialkylamino, alkylheterocyclyl, alkylaryl, alkylheteroaryl, amido, aryl, alkoxyoxo, halo, heteroaryl, heterocyclyl, cyano, oxo, or aminoalkyl wherein each of said alkyl, alkoxy, alkoxyalkylamino, amino, alkylamino, dialkylamino, alkylheterocyclyl, alkylaryl, alkylheteroaryl, aryl, alkoxyoxo, heteroaryl, heterocyclyl and aminoalkyl is either unsubstituted or optionally independently substituted with 1-3 independently selected $P^1$ substituents, where $P^1$ is alkyl, aryl, heteroaryl, heterocyclyl, cycloalkyl, alkoxy, amino, alkylamino, dialkylamino, or alkylthio, or two $P^1$ adjacent moieties together form an alkylenedioxy moiety fused to said aryl, heteroaryl, heterocyclyl ring they are attached to.

3. The compound of claim 1, wherein $R^{23}$ is

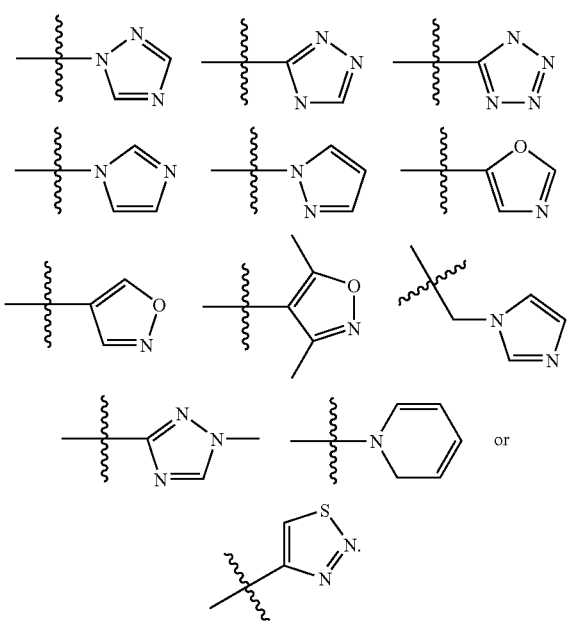

4. The compound of claim 1, wherein $R^{23}$ is

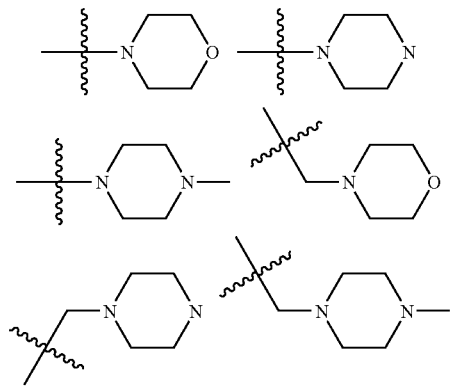

-continued

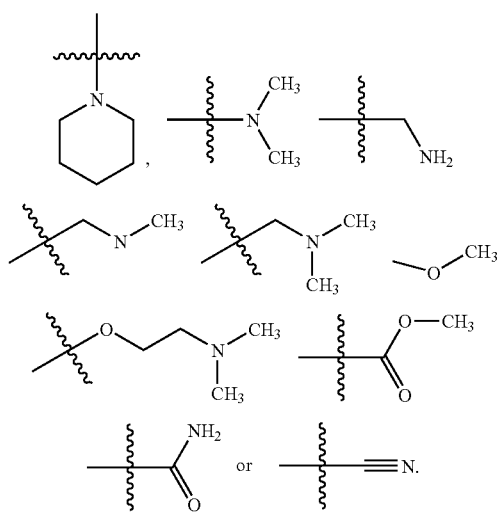

5. The compound of claim 1, wherein:

R$^{24}$ is hydrogen, halo, alkyl, alkylene, lower alkyl, aryl, heteroaryl, heterocyclyl, alkoxy, amino, aminoalkyl, alkylamino, dialkylamino, alkylthio, trihaloalkyl, wherein each of said alkyl, alkylene, lower alkyl, aryl, heteroaryl, heterocyclyl, alkoxy, amino, aminoalkyl, alkylamino, dialkylamino, alkylthio, trihaloalkyl is unsubstituted or optionally independently substituted with 1-3 independently selected P$^1$ substituents, where P$^1$ is alkyl, aryl, heteroaryl, heterocyclyl, cycloalkyl, alkoxy, amino, alkylamino, dialkylamino, or alkylthio; or two R$^{24}$ groups, which substitute atoms in a 1,2 or 1,3 arrangement on the phenyl ring said R$^{24}$ is shown attached to together form —O—(CH$_2$)$_y$—O—, —S—(CH$_2$)$_y$—O—, —S—(CH$_2$)$_y$—S, —CH=CH—CH=N—, —N=CH—CH=N—, or —S—CH=N— where y is 1 or 2.

6. The compound of claim 1, wherein R$^{23}$ and R$^{24}$ together form a ring moiety with said ring moiety being fused to the phenyl ring they are shown attached to, such that R$^{20}$ becomes:

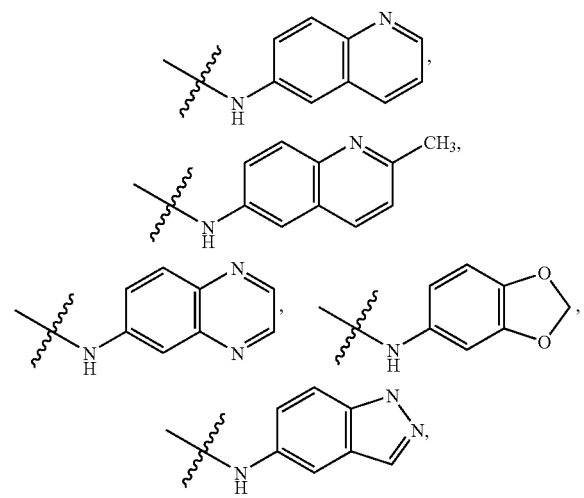

7. The compound of claim 1, wherein R$^{25}$ and R$^{26}$ are linked together to form a six-membered heterocyclyl or heteroaryl, and R$^<$ is:

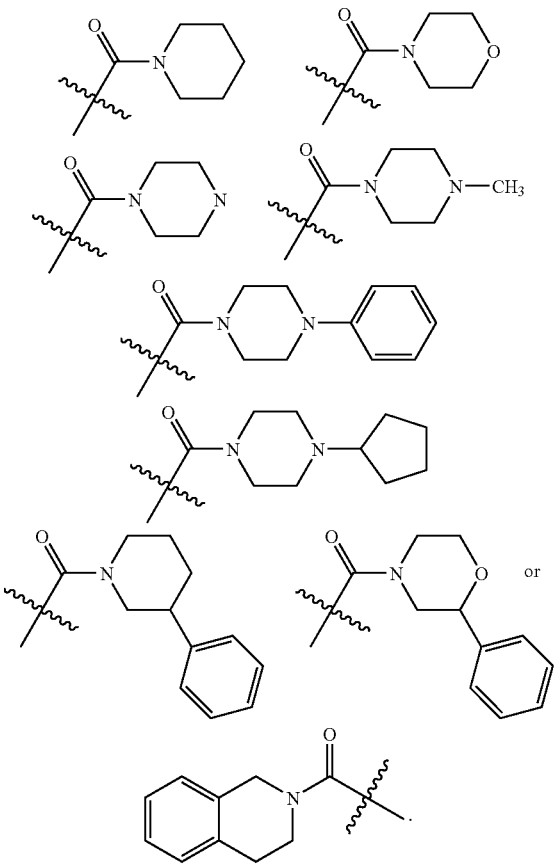

8. A pharmaceutical composition comprising a therapeutically effective amount of at least one compound of claim 1, or a pharmaceutically acceptable salt, or ester thereof, in combination with at least one pharmaceutically acceptable carrier.

9. The pharmaceutical composition of claim 8, additionally comprising one or more anti-cancer agents selected from the group consisting of cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, gefitinib, erlotinib hydrochloride, antibodies to EGFR, imatinib, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine.

10. A compound of claim 1 in purified form.

\* \* \* \* \*

UNITED STATES PATENT AND TRADEMARK OFFICE
CERTIFICATE OF CORRECTION

PATENT NO.       : 7,446,195 B2
APPLICATION NO.  : 11/505263
DATED            : November 4, 2008
INVENTOR(S)      : Deng et al.

It is certified that error appears in the above-identified patent and that said Letters Patent is hereby corrected as shown below:

Claim 6, col. 113, line 43: Please correct "claim 1" to --claims 1-5--.

Claim 7, col. 114, line 21: Please correct "R<" to --R21--.

Claim 8, col. 114, line 60: Please correct "salt, or ester" to --salt, solvate or ester--.

Signed and Sealed this

Third Day of March, 2009

JOHN DOLL
*Acting Director of the United States Patent and Trademark Office*